(12) United States Patent
Kurtz

(10) Patent No.: US 8,764,736 B2
(45) Date of Patent: *Jul. 1, 2014

(54) LASER-INDUCED PROTECTION SHIELD IN LASER SURGERY

(75) Inventor: Ronald M. Kurtz, Irvine, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 1196 days.

This patent is subject to a terminal disclaimer.

(21) Appl. No.: 12/205,839

(22) Filed: Sep. 5, 2008

(65) Prior Publication Data

US 2009/0143772 A1 Jun. 4, 2009

Related U.S. Application Data

(60) Provisional application No. 60/970,214, filed on Sep. 5, 2007.

(51) Int. Cl.
*A61B 18/20* (2006.01)
*A61F 9/008* (2006.01)

(52) U.S. Cl.
USPC .......................................................... 606/4

(58) Field of Classification Search
None
See application file for complete search history.

(56) References Cited

U.S. PATENT DOCUMENTS

| | | |
|---|---|---|
| 4,481,948 A | 11/1984 | Sole |
| 4,538,608 A | 9/1985 | L'Esperace, Jr. |
| 4,554,917 A | 11/1985 | Tagnon |
| 4,633,866 A | 1/1987 | Peyman et al. |
| 4,638,801 A | 1/1987 | Daly et al. |
| 4,686,366 A | 8/1987 | Stuke |
| 4,694,828 A | 9/1987 | Eichenbaum |
| 4,766,896 A | 8/1988 | Pao |
| 4,888,015 A | 12/1989 | Domino |
| 4,907,586 A | 3/1990 | Bille et al. |
| 5,013,319 A | 5/1991 | Davis |
| 5,036,592 A | 8/1991 | Marshall |
| 5,089,022 A | 2/1992 | Koester et al. |
| 5,139,022 A | 8/1992 | Lempert |
| 5,225,862 A | 7/1993 | Nagano et al. |
| 5,246,435 A | 9/1993 | Bille et al. |
| 5,261,923 A | 11/1993 | Soares |
| 5,269,787 A | 12/1993 | Cozean, Jr. et al. |
| 5,333,018 A | 7/1994 | Heine et al. |
| 5,336,215 A | 8/1994 | Hsueh et al. |
| 5,423,841 A | 6/1995 | Kornefeld |
| 5,439,462 A | 8/1995 | Bille et al. |
| 5,442,412 A | 8/1995 | Frey et al. |
| 5,520,679 A | 5/1996 | Lin |
| 5,549,632 A | 8/1996 | Lai |
| 5,656,186 A | 8/1997 | Mourou et al. |
| 5,669,923 A | 9/1997 | Gordon |
| 5,738,677 A | 4/1998 | Colvard et al. |
| 5,957,921 A | 9/1999 | Mirhashemi et al. |
| 5,968,095 A | 10/1999 | Norrby |
| 5,984,916 A | 11/1999 | Lai |
| 5,987,151 A | 11/1999 | Akashi |
| 5,993,438 A | 11/1999 | Juhasz et al. |
| 6,004,314 A | 12/1999 | Wei et al. |
| 6,010,497 A | 1/2000 | Tang et al. |
| 6,066,138 A | 5/2000 | Sheffer et al. |
| 6,099,522 A | 8/2000 | Knopp et al. |
| 6,146,375 A | 11/2000 | Juhasz et al. |
| 6,165,190 A | 12/2000 | Nguyen |
| 6,197,018 B1 | 3/2001 | O'Donnell, Jr. |
| 6,217,570 B1 | 4/2001 | Nevyas |
| 6,254,595 B1 | 7/2001 | Juhasz et al. |
| 6,322,556 B1 | 11/2001 | Gwon et al. |
| 6,328,732 B1 | 12/2001 | Donitzky et al. |
| 6,344,040 B1 | 2/2002 | Juhasz et al. |
| RE37,585 E | 3/2002 | Mourou et al. |
| 6,379,005 B1 | 4/2002 | Williams et al. |
| 6,391,020 B1 | 5/2002 | Kurtz et al. |
| 6,409,718 B1 | 6/2002 | Tang |
| 6,451,006 B1 | 9/2002 | Bille |
| 6,454,761 B1 | 9/2002 | Freedman |
| 6,508,812 B1 | 1/2003 | Williams et al. |
| 6,579,282 B2 | 6/2003 | Bille et al. |
| 6,610,051 B2 | 8/2003 | Bille |
| 6,620,160 B2 | 9/2003 | Lewis et al. |
| 6,623,476 B2 | 9/2003 | Juhasz et al. |
| 6,676,653 B2 | 1/2004 | Juhasz et al. |

(Continued)

FOREIGN PATENT DOCUMENTS

| | | |
|---|---|---|
| EP | 1252872 | 10/2002 |
| EP | 1 302 186 | 4/2003 |

(Continued)

OTHER PUBLICATIONS

European Supplementary Search Report for European Application No. 08843434, mailed Dec. 16, 2010.
European Supplementary Search Report for European Application No. 09700876.7, mailed Aug. 10, 2011, 3 pages.
International Search Report and Written Opinion dated Feb. 17, 2012 for International Application No. PCT/US2011/041677.
International Search Report and Written Opinion dated Feb. 17, 2012 for International Application No. PCT/US2011/041700.
Toyran S. et al., 2005, "Femtosecond laser photodisruption of human trabecular meshwork: an in vitro study", Experimental Eye Research, vol. 81, 298-305.
Chinn, S.R., et al., "Optical coherence tomography using a frequency-tunable optical source," *Optics Letters*, 22(5):340-342, Mar. 1997.

(Continued)

*Primary Examiner* — Robert A. Wax
*Assistant Examiner* — H. Sarah Park

(57) ABSTRACT

Techniques, apparatus and systems for laser surgery are described to provide protection of sensitive tissues from surgical laser pulses. For example, an ophthalmic surgical method may include determining a surgical target region in an eye, selecting a protection region between the surgical target region and a photosensitive tissue, estimating a damage-threshold of the photosensitive tissue and a protection-threshold of the protection region, applying preliminary laser-pulses to the protection region with parameters between the damage-threshold and the protection threshold to form a protection barrier, and applying surgical laser pulses to the surgical target region.

15 Claims, 28 Drawing Sheets

(56) References Cited

U.S. PATENT DOCUMENTS

| | | | |
|---|---|---|---|
| 6,712,809 B2 | 3/2004 | Li et al. |
| 6,726,679 B1 | 4/2004 | Dick et al. |
| 6,730,074 B2 | 5/2004 | Bille et al. |
| 6,751,033 B2 | 6/2004 | Goldstein et al. |
| 6,863,667 B2 | 3/2005 | Webb et al. |
| 6,899,707 B2 | 5/2005 | Scholler et al. |
| 6,902,561 B2 | 6/2005 | Kurtz et al. |
| 6,913,603 B2 | 7/2005 | Knopp et al. |
| 6,986,763 B2 | 1/2006 | Holmén |
| 6,991,629 B1 | 1/2006 | Juhasz et al. |
| 7,018,376 B2 | 3/2006 | Webb et al. |
| 7,027,233 B2 | 4/2006 | Goldstein et al. |
| 7,044,602 B2 | 5/2006 | Chernyak |
| 7,101,364 B2 | 9/2006 | Bille |
| 7,131,968 B2 | 11/2006 | Bendett et al. |
| 7,284,858 B2 | 10/2007 | Bergner et al. |
| 7,371,230 B2 | 5/2008 | Webb et al. |
| 7,390,089 B2 | 6/2008 | Loesel et al. |
| 7,391,520 B2 | 6/2008 | Zhou et al. |
| 7,402,159 B2 | 7/2008 | Loesel et al. |
| 7,742,173 B2 | 6/2010 | Yun et al. |
| 2002/0013574 A1 | 1/2002 | Elbrecht et al. |
| 2002/0097374 A1* | 7/2002 | Payne et al. ............... 351/200 |
| 2002/0133145 A1 | 9/2002 | Gerlach et al. |
| 2002/0193704 A1 | 12/2002 | Goldstein et al. |
| 2003/0073983 A1* | 4/2003 | Bille ............................. 606/5 |
| 2004/0044355 A1 | 3/2004 | Nevyas |
| 2004/0102765 A1 | 5/2004 | Koenig |
| 2004/0106929 A1 | 6/2004 | Masket |
| 2004/0151466 A1 | 8/2004 | Crossman-Bosworth et al. |
| 2004/0199149 A1* | 10/2004 | Myers et al. ................. 606/4 |
| 2004/0243111 A1 | 12/2004 | Bendett et al. |
| 2004/0243112 A1 | 12/2004 | Bendett et al. |
| 2004/0243113 A1 | 12/2004 | Sugiura et al. |
| 2004/0243233 A1 | 12/2004 | Phillips |
| 2004/0254568 A1 | 12/2004 | Rathjen |
| 2005/0015120 A1 | 1/2005 | Seibel et al. |
| 2005/0081393 A1 | 4/2005 | Su et al. |
| 2005/0090813 A1 | 4/2005 | Schweitzer et al. |
| 2005/0107773 A1 | 5/2005 | Bergt et al. |
| 2005/0165387 A1 | 7/2005 | Lubatschowski et al. |
| 2005/0173817 A1 | 8/2005 | Fauver et al. |
| 2005/0245915 A1 | 11/2005 | Loesel et al. |
| 2005/0284774 A1 | 12/2005 | Mordaunt |
| 2005/0286019 A1 | 12/2005 | Wiltberger et al. |
| 2005/0288745 A1 | 12/2005 | Andersen et al. |
| 2006/0020172 A1 | 1/2006 | Luerssen et al. |
| 2006/0100613 A1 | 5/2006 | McArdle et al. |
| 2006/0179992 A1 | 8/2006 | Kermani |
| 2006/0187462 A1 | 8/2006 | Srinivasan et al. |
| 2006/0192921 A1 | 8/2006 | Loesel et al. |
| 2006/0195076 A1* | 8/2006 | Blumenkranz et al. ........... 606/4 |
| 2006/0217688 A1 | 9/2006 | Lai |
| 2006/0235428 A1 | 10/2006 | Silvestrini |
| 2006/0264990 A1 | 11/2006 | Michelson et al. |
| 2007/0121069 A1 | 5/2007 | Andersen et al. |
| 2007/0126985 A1 | 6/2007 | Wiltberger et al. |
| 2007/0129709 A1 | 6/2007 | Andersen et al. |
| 2007/0129775 A1 | 6/2007 | Mordaunt et al. |
| 2007/0147730 A1 | 6/2007 | Wiltberger et al. |
| 2007/0173759 A1 | 7/2007 | Augustine et al. |
| 2007/0173794 A1 | 7/2007 | Frey et al. |
| 2007/0173795 A1* | 7/2007 | Frey et al. .................... 606/5 |
| 2007/0185475 A1 | 8/2007 | Frey et al. |
| 2007/0189664 A1 | 8/2007 | Andersen et al. |
| 2007/0230520 A1 | 10/2007 | Mordaunt et al. |
| 2008/0033406 A1 | 2/2008 | Andersen et al. |
| 2008/0049188 A1 | 2/2008 | Wiltberger et al. |
| 2008/0071254 A1 | 3/2008 | Lummis et al. |
| 2008/0088795 A1 | 4/2008 | Goldstein et al. |
| 2008/0281303 A1 | 11/2008 | Culbertson et al. |
| 2008/0281413 A1 | 11/2008 | Culbertson et al. |
| 2008/0319427 A1 | 12/2008 | Palanker |
| 2009/0012507 A1 | 1/2009 | Culbertson et al. |
| 2009/0048586 A1 | 2/2009 | Krueger et al. |
| 2009/0088734 A1 | 4/2009 | Mordaunt |
| 2009/0137988 A1 | 5/2009 | Kurtz |
| 2009/0137991 A1 | 5/2009 | Kurtz |
| 2009/0137993 A1 | 5/2009 | Kurtz |
| 2009/0149840 A1 | 6/2009 | Kurtz |
| 2009/0149841 A1 | 6/2009 | Kurtz |
| 2009/0171327 A1 | 7/2009 | Kurtz et al. |
| 2009/0177189 A1 | 7/2009 | Raksi |
| 2010/0004641 A1 | 1/2010 | Frey et al. |
| 2010/0004643 A1 | 1/2010 | Frey et al. |
| 2010/0022994 A1 | 1/2010 | Frey et al. |
| 2010/0022995 A1 | 1/2010 | Frey et al. |
| 2010/0022996 A1 | 1/2010 | Frey et al. |
| 2010/0042079 A1 | 2/2010 | Frey et al. |
| 2010/0110377 A1 | 5/2010 | Maloca et al. |
| 2010/0324542 A1 | 12/2010 | Kurtz et al. |
| 2010/0324543 A1 | 12/2010 | Kurtz et al. |

FOREIGN PATENT DOCUMENTS

| | | |
|---|---|---|
| KR | 2002-0093935 | 12/2002 |
| WO | 98/27863 | 7/1998 |
| WO | 03/022168 | 3/2003 |
| WO | 2006/074469 | 7/2006 |
| WO | 2007/103349 | 9/2007 |

OTHER PUBLICATIONS

Freel, C., et al., "Analysis of nuclear fiber cell compaction in transparent and cataractous diabetic human lenses by scanning electron microscopy," *BMC Ophthalmology*, 3(1):1-9, Jan. 2003.

Heys, K.R., et al., "Massive increase in the stiffness of the human lens nucleus with age: the basis for presbyopia?" *Molecular Vision*, 10:956-963, Dec. 2004.

Huber, R., et al., "Three-dimensional and C-mode OCT imaging with a compact, frequency swept laser source at 1300 nm," *Optics Express*, 13(26):10523-10538, Dec. 2005.

International Search Report and Written Opinion dated Sep. 13, 2010 for International Application No. PCT/US2009/069510, filed Sep. 18, 2008 (13 pages).

Sweeney, M.H.J., et al., "An Impediment to Glutathione Diffusion in Older Normal Human Lenses: a Possible Precondition for Nuclear Cataract," *Experimental Eye Research*, 67(5):587-595, Nov. 1998.

Yun, S.H., et al., "Wavelength-Swept Fiber Laser with Frequency Shifted Feedback and Resonantly Swept Intra-Cavity Acoustooptic Tunable Filter," IEEE Journal of Selected Topics in Quantum Electronics, 3(4):1087-1096, Aug. 1997.

Hammer, D., et al., "Shielding properties of laser-induced breakdown in water for pulse durations from 5 ns To 125 fs," *Applied Optics*, 36(22):5630-5640, Aug. 1997.

Vogel, A., et al., "Intraocular Photodisruption with Picosecond and Nanosecond Laser Pulses: Tissue Effects in Cornea, Lens, and Retina," *Ophthalmology & Visual Science*, 35(7):3032-3044, Jun. 1994.

International Search Report and Written Opinion dated Jul. 31, 2009 for International Application No. PCT/US2009/030676, filed Jan. 9, 2009 (9 pages).

International Search Report and Written Opinion dated Jun. 30, 2009 for International Application No. PCT/US2008/082156, filed Oct. 31, 2008 (9 pages).

International Search Report and Written Opinion dated Mar. 12, 2009 for International Application No. PCT/US2008/075506, filed Sep. 5, 2008 (10 pages).

International Search Report and Written Opinion dated Mar. 18, 2009 for International Application No. PCT/US2008/076890, filed Sep. 18, 2008 (8 pages).

International Search Report and Written Opinion dated Mar. 27, 2009 for International Application No. PCT/US2008/075911, filed Sep. 10, 2008 (9 pages).

International Search Report and Written Opinion dated Mar. 30, 2009 for International Application No. PCT/US2008/076910, filed Sep. 18, 2008 (9 pages).

(56) References Cited

OTHER PUBLICATIONS

International Search Report and Written Opinion dated Mar. 17, 2009 for International Application No. PCT/US2008/075509, filed Sep. 5, 2008 (10 pages).

Erpelding T N et al., "Bubble-based acoustic radiation force for monitoring intraocular lens elasticity", 2004 IEEE Ultrasonics Symposium, vol. 1, pp. 732-735, Aug. 2004.

European Examination Report dated Nov. 26, 2012 for European Application No. 08829584.5, 6 pages.

* cited by examiner

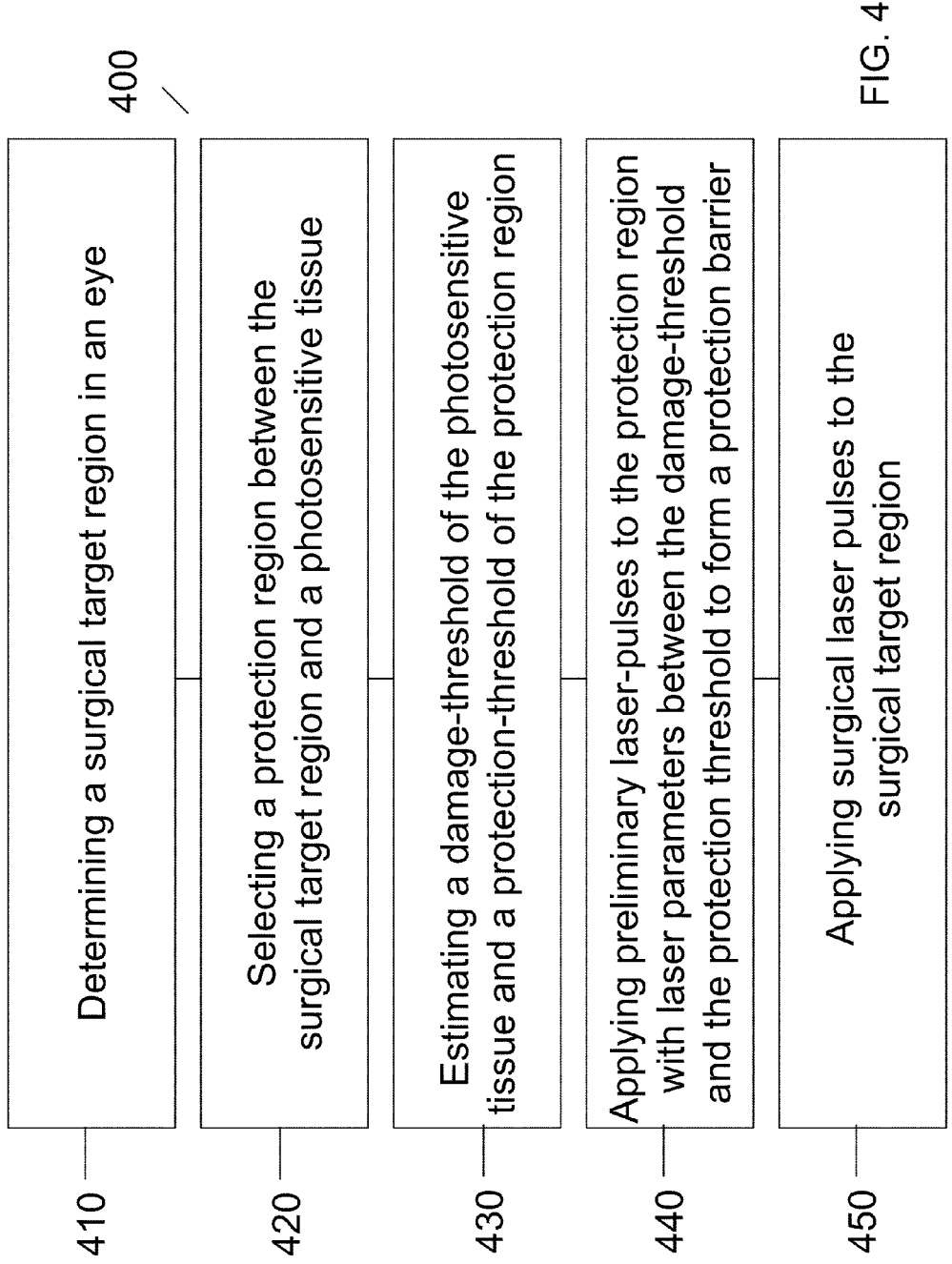

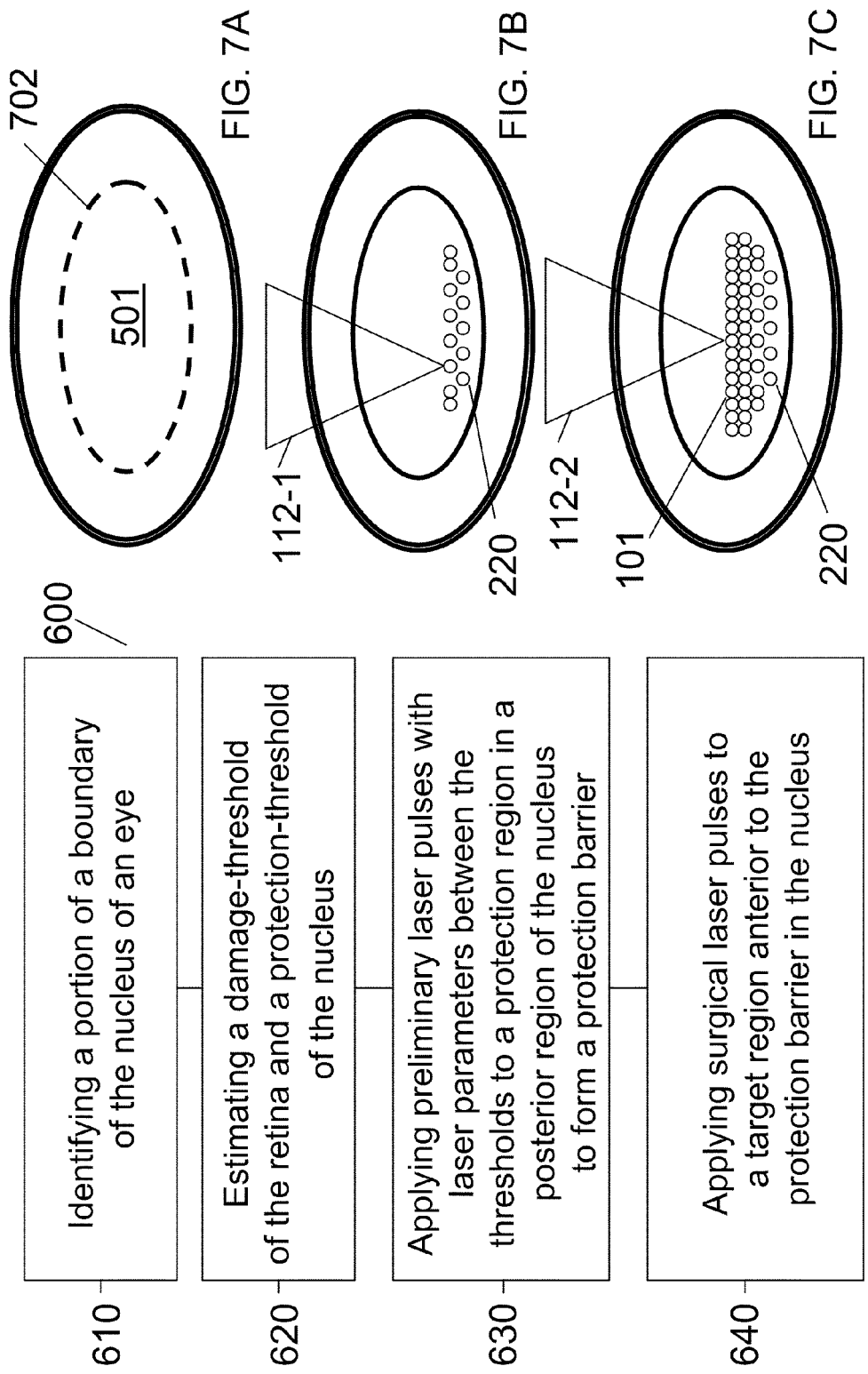

Diagnostic Mode

Surgical Mode

LASER-INDUCED PROTECTION SHIELD IN LASER SURGERY

CROSS-REFERENCE TO RELATED APPLICATION

This application claims priority to and benefit of U.S. provisional application Ser. No. 60/970,214, entitled, "Laser-Induced Protection Shield in Laser Ophthalmic Surgery", and filed on Sep. 5, 2007, which is incorporated herein by reference in its entirety.

BACKGROUND

This application relates to laser surgery including laser ophthalmic surgery.

Laser-induced photodisruption is widely used in laser ophthalmic surgery. Various ophthalmic laser surgical systems based on photodisruption use relatively long pulse duration lasers in single shot or burst modes. For example, an Nd:YAG laser may be used to generate a laser beam with a series of a few pulses, e.g., approximately three sequential laser pulses in some procedures. In surgical procedures using such laser devices the average laser power of the surgical laser beam delivered to the eye is low and the average power of the residual light of the surgical laser beam that reaches the retina or other structures in the eye can be below the threshold power level that can cause injury to the retina or other structures.

In some surgical procedures, even if hundreds of laser pulses are placed, these are often placed with a lower precision, e.g., on the order of hundreds of microns.

Thus, laser pulses often have low impact energy and are sufficiently widely spaced so that the risk of thermal or photic injury to the retina and other structures adjacent to an intended surgical target by such laser pulses is low and no special precautions for protecting the retina may be required when operating these laser surgical systems.

SUMMARY

Techniques, apparatus and systems for laser surgery are described to provide protection of sensitive tissues from surgical laser pulses.

In one aspect, an ophthalmic surgical method may include determining a surgical target region in an eye, selecting a protection region between the surgical target region and a photosensitive tissue, estimating a damage-threshold of the photosensitive tissue and a protection-threshold of the protection region, applying preliminary laser-pulses to the protection region with parameters between the damage-threshold and the protection threshold to form a protection barrier, and applying surgical laser pulses to the surgical target region.

The selecting the protection region may include selecting a location and shape of the protection region so that a protection barrier formed in the protection region is capable of protecting the photosensitive tissue from damage by residual surgical laser pulses.

The protecting the photosensitive tissue may include blocking, scattering, or absorbing the residual surgical laser pulses.

The selecting the protection region may include determining a portion of a boundary of a nucleus of the eye.

The estimating the damage-threshold of the photosensitive tissue may include estimating damage-threshold laser parameters, wherein laser pulses applied with the damage-threshold laser parameters are capable of damaging the photosensitive tissue.

The estimating the protection-threshold of the protection region may include estimating protection-threshold laser parameters, wherein laser pulses applied with the protection-threshold laser parameters are capable of forming a protection barrier in the protection region.

The estimating the protection-threshold and the damage-threshold may include analyzing characteristics of elements of a surgical laser system, preparatory and pre-operative measurements, observations of the eye of the patient, using calculations, using an age-based algorithm, using data obtained form cadaver experiments, and consulting data-bases.

The estimating the damage-threshold and the protection-threshold may include estimating a laser pulse energy in the range of 0.5 microJ to 50 microJ, estimating a duration of a laser pulse in the range of 0.01 picoseconds to 50 picoseconds, estimating a frequency of applying laser pulses in the range of 10 kHz to 100 MHz, and estimating a separation distance of target regions of laser pulses in the range of 1 micron to 50 microns.

The applying the preliminary laser-pulses with parameters between the damage-threshold and the protection threshold may include applying the preliminary laser pulses with laser parameters suitable to avoid damaging the photosensitive tissue.

In some implementations, an eye-surgery method may include identifying a portion of a boundary of a nucleus in a lens of an eye, estimating a damage-threshold of a retina and a protection-threshold of the nucleus, applying preliminary laser pulses with laser parameters between the damage-threshold and the protection-threshold to a protection region in a posterior region of the nucleus to form a protection barrier, and applying surgical laser pulses to a target region anterior to the protection barrier in the nucleus.

The identifying the portion of the boundary of the nucleus may include generating spaced-apart probe-bubbles inside the lens, observing a property of the generated probe-bubbles, identifying the portion of the boundary in connection to the observed property of the probe-bubbles.

The observing a property of the generated bubbles may include identifying one or more probe-bubbles exhibiting a first growth rate, and identifying one or more probe-bubbles exhibiting a second growth rate different from the first growth rate, and the identifying the portion of the boundary may include identifying a boundary between the probe-bubbles exhibiting the first growth rate and the probe-bubbles exhibiting the second growth rate.

The observing a property of the generated probe-bubbles may include applying ultrasound to the lens, identifying one or more probe-bubbles exhibiting a first response to the ultrasound, and identifying one or more probe-bubbles exhibiting a second response different from the first response, and the identifying the portion of the boundary may include identifying a boundary between the probe-bubbles exhibiting the first response and the probe-bubbles exhibiting the second response.

The identifying the boundary may include observing the probe-bubbles with an optical imaging method, and observing the probe-bubbles with an optical coherence tomography.

The identifying the boundary may include a preoperative and an intra-operative identification of the boundary, consulting a data-base correlating the boundary of the nucleus with a measurable characteristic of the eye, performing a calculation based on a measurable characteristic, and performing an age-based determination of the boundary.

The estimating the damage-threshold of the retina may include estimating damage-threshold laser parameters, wherein laser pulses applied with the damage-threshold laser parameters are capable of damaging the retina.

The estimating the protection-threshold of the nucleus may include estimating protection-threshold laser parameters, wherein laser pulses applied with the protection-threshold laser parameters to the protection region are capable of forming a protection barrier.

The estimating a protection-threshold and a damage-threshold may include analyzing characteristics of elements of a surgical laser system, preparatory and pre-operative measurements, observations of the eye of the patient, using calculations, using an age-based algorithm, cadaver experiments, and consulting data-bases.

The estimating the damage-threshold and the protection-threshold may include estimating a laser pulse energy in the range of 0.5 microJ to 50 microJ, estimating a duration of a laser pulse in the range of 0.01 picoseconds to 50 picoseconds, estimating a frequency of applying laser pulses in the range of 10 kHz to 100 MHz, and estimating a separation distance of target regions of laser pulses in the range of 1 micron to 50 microns.

The applying the preliminary laser pulses may include applying the preliminary laser pulses with laser parameters ensuring that the preliminary laser pulses damage the retina only to an insubstantial degree, and forming the protection barrier so situated and shaped that it is capable of protecting the retina from residual surgical laser pulses.

The applying surgical laser pulses may include disrupting, fragmenting, and emulsifying a portion of the nucleus.

Implementations include a laser system for fragmenting the crystalline lens of an eye, including a pulsed laser configured to generate a laser beam of laser pulses, and a laser controller, configured to control the pulsed laser to apply preliminary laser-pulses to a protection region in the eye with parameters between a damage-threshold of a photosensitive tissue and a protection-threshold of the protection region to form a protection barrier, and to apply surgical laser pulses to a surgical target region.

The laser controller may be configured to control the pulsed laser to generate laser pulses with an energy in the range of approximately 0.5 microJ to 50 microJ, a separation of adjacent target areas in the range of approximately 1 micron to 50 microns, a duration in the range of approximately 0.01 picoseconds to 50 picoseconds, and a repetition rate in the range of 10 kHz to 100 MHz.

The laser system further may include an optical system, configured to observe a property of probe-bubbles, generated in a lens of the eye, and a processor, configured to identify a nucleus within the lens using the observed property of the probe-bubbles.

Implementations may include a surgical method for protecting a photosensitive tissue distal to a target of photodisruption, including determining a surgical target region in a body of a subject, selecting a protection region between the surgical target region and the photosensitive tissue, estimating a damage-threshold of the photosensitive tissue and a protection-threshold of the protection region, applying preliminary laser-pulses to the protection region with parameters between the damage-threshold and the protection threshold to form a protection barrier, and applying surgical laser pulses to the surgical target region.

Other implementations include the following. One implementation if a method for protecting retina in laser surgery that includes selecting a surgical target region in an eye and directing a preliminary laser beam of one or more preliminary laser pulses into the eye to focus the preliminary laser beam at or near a region in the eye between the selected surgical target region and the retina or in the posterior region of the selected surgical target region to create photodisruption without damaging the retina or an adjacent sensitive tissue. The photodisruption byproduct caused by the one or more preliminary laser pulses in the region forms a protection region between the selected surgical target and the retina. In this method, subsequent to delivery of the preliminary laser beam, a surgical laser beam of one or more surgical laser pulses is directed to the selected surgical target region to perform surgery.

Another implementation is a method for protecting sensitive tissue distal to an intended target of photodisruption. This method includes selecting a surgical target region in a body of a subject and directing a preliminary laser beam of one or more preliminary laser pulses into the body to focus the preliminary laser beam at or near a region in the body between the selected surgical target region and the sensitive tissue or in a region of the selected surgical target region optically closest to the sensitive tissue to create photodisruption without damaging the sensitive tissue. Photodisruption byproduct caused by the one or more preliminary laser pulses in the region forms a protection region between the selected surgical target and the sensitive tissue. Subsequent to delivery of the preliminary laser beam, a surgical laser beam of one or more surgical laser pulses is directed to the selected surgical target region to perform surgery.

Another implementation is a laser surgical system for performing laser surgery that includes means for selecting a surgical target region in an eye; means for producing a preliminary laser beam of one or more preliminary laser pulses which are operable to create photodisruption in a region in the eye without damaging the retina or an adjacent sensitive tissue; and means for directing the preliminary laser beam into the eye to focus the preliminary laser beam at or near a region in the eye between the selected surgical target region and the retina or in a region of the selected surgical target region optically closest to the sensitive tissue to create photodisruption. Photodisruption byproduct caused by the one or more preliminary laser pulses in the region forms a protection region between the selected surgical target and the retina. This system also includes means for producing and directing a surgical laser beam of one or more surgical laser pulses to the selected surgical target region to perform surgery subsequent to delivery of the preliminary laser beam.

Yet another implementation is a laser surgical system for performing laser surgery that includes a laser source operable to produce laser pulses, the laser being adjustable to vary parameters of the produced laser pulses; an optics module to receive the laser pulses from the laser source and to guide and direct the laser pulses to a surgical target on a body of a subject under surgery; a monitor unit positioned to monitor a location of the laser pulses on the subject; and a controller in communication with the laser source and the optics module to control the laser source and the optics module. The controller is operable to control the laser source to operate in a first mode where laser parameters of the laser pulses are set to produce photodisruption on the subject without causing damage to a sensitive tissue distal to a location where the laser pulses are directed, and a second mode where laser parameters of the laser pulses are set to produce surgical operations on the subject by damaging a tissue at a location where the laser pulses are directed. The controller is operable to control the optics module to adjust direction and location of the laser pulses, based information from monitor unit, to place laser pulses produced by the laser source in the first mode at a location between a surgical target and sensitive tissue to produce a protective photodisruption region and subsequently to place laser pulsed produced by the laser source in the second mode at the surgical target.

These and other features are described in greater detail in the description, the drawings and the claims.

BRIEF DESCRIPTION OF FIGURES

FIG. 4 illustrates the steps of an exemplary ophthalmic surgical procedure with the introduction of a protection region.

FIG. 6 illustrates an example of an ophthalmic surgical procedure.

FIGS. 7A-C illustrate an embodiment of the procedure of FIG. 6.

DETAILED DESCRIPTION

Figure 1:
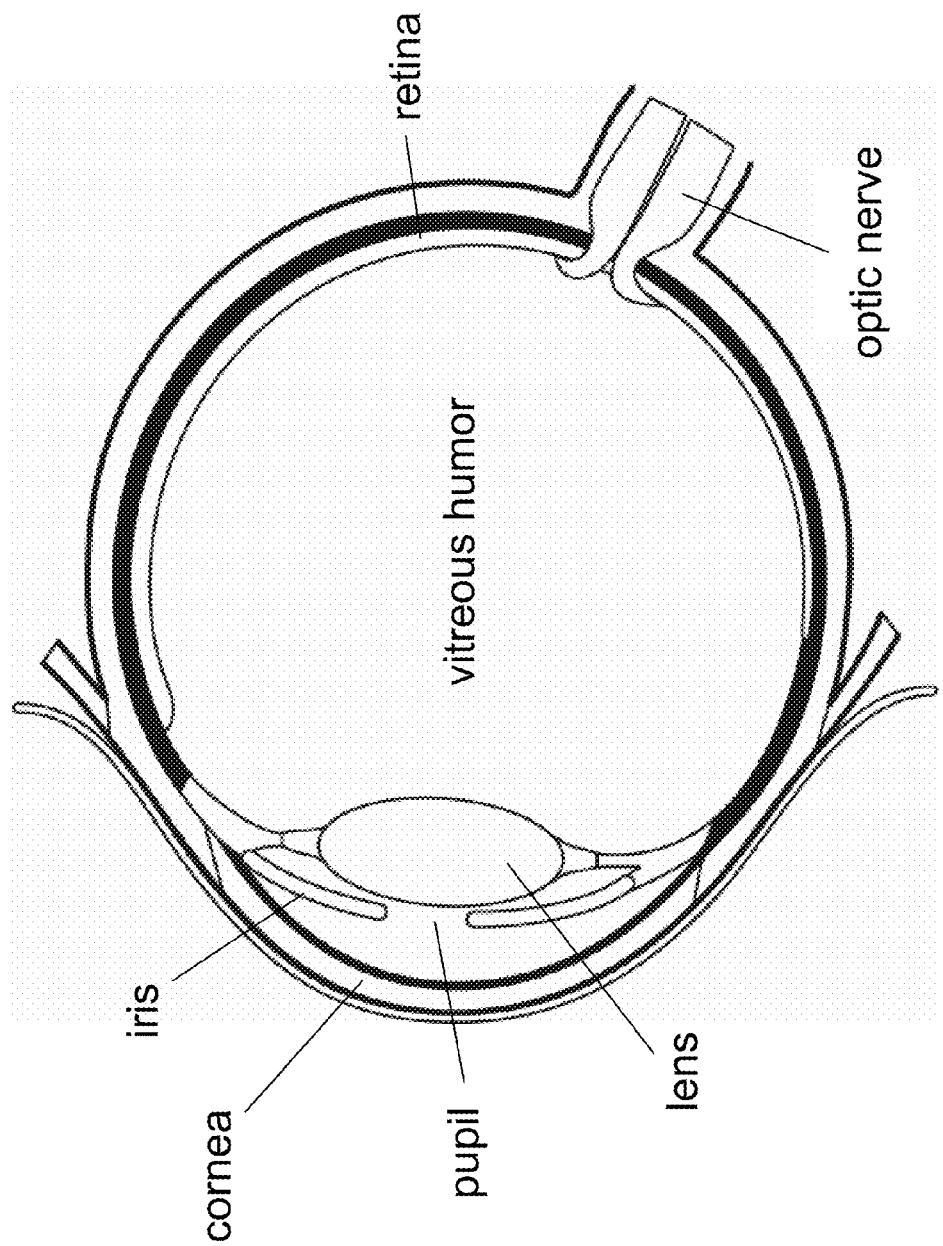
FIG. 1 illustrates an overview of an eye.

FIG. 1 illustrates the overall structure of the eye. The incident light propagates through the optical path which includes the cornea, the anterior chamber, the pupil, the posterior chamber, the lens and the vitreous humor. These optical elements guide the light on the retina.

Various ophthalmic laser surgical systems use high repetition rate lasers with a lower pulse energy level to achieve more precise control of the targeting of the laser, e.g., microns or tens of microns. In these procedures the high repetition rates may deliver relatively high average power to the target and adjacent structures. Only a portion of the delivered optical energy of a laser pulse is absorbed in the surgical target region. Therefore, the non-absorbed, or residual laser light can continue to propagate in the eye to reach deeper structures in the eye and may damage one or more other structures in the eye that are not the intended surgical target.

For example, the retina in the back of the eye is a sensitive structure due to its highly absorbing nature in the visible and other wavelengths of light. Therefore, in the above described high repetition rate laser surgical systems, there is a potential risk that the residual light that is not absorbed in the surgical target region can reach the retina and damage it. For example, in corneal or lens surgery, the residual light may reach the retina at a dangerously high power level after passing the structures between the cornea and retina, including the iris and lens. In addition, inadvertent focusing of these multiple pulses might also directly damage sensitive structures that are not intended targets.

This application describes implementations of a protective technique that reduces the risk of damaging the retina or other sensitive non-targeted structures within the eye by the residual light in high average power photodisruptive laser ophthalmic surgery systems. In addition, the present protective technique can also be implemented to reduce the risk of direct damage from photodisruption beyond the intended target.

The described protective method can be also implemented in other photosensitive areas of the body, not just the eye.

In some implementations, prior to the application of surgical laser pulses, preliminary laser pulses can be focused to a protection region between the surgical target region and the retina or another sensitive target, in order to cause photodisruption in the protection region. This process may create a photodisruption byproduct to serve as a protection barrier.

For example, a set of cavitation bubbles may be created by laser in the protection region as a protection barrier before performing an ophthalmic surgery. The laser-induced protection barrier scatters or absorbs light and thus provides a protection shield for the retina or another sensitive tissue against inadvertent photodisruption by the light used during the ophthalmic procedure.

After the application of the preliminary pulses to form the protection barrier or shield, surgical pulses can be applied to the surgical target region to perform a photodisruptive surgery. In some situations, the preliminary laser pulses may be directed to the surgical target region so as to form the protection barrier within the surgical target or adjacent to its boundary. The pulse parameters of the preliminary laser pulses, such as energy, repetition rate, spot separation and others can be chosen to minimize the risk of damaging the retina or another sensitive tissue. After the preliminary pulses, surgical laser pulses can be delivered to perform the surgery.

Figure 2:
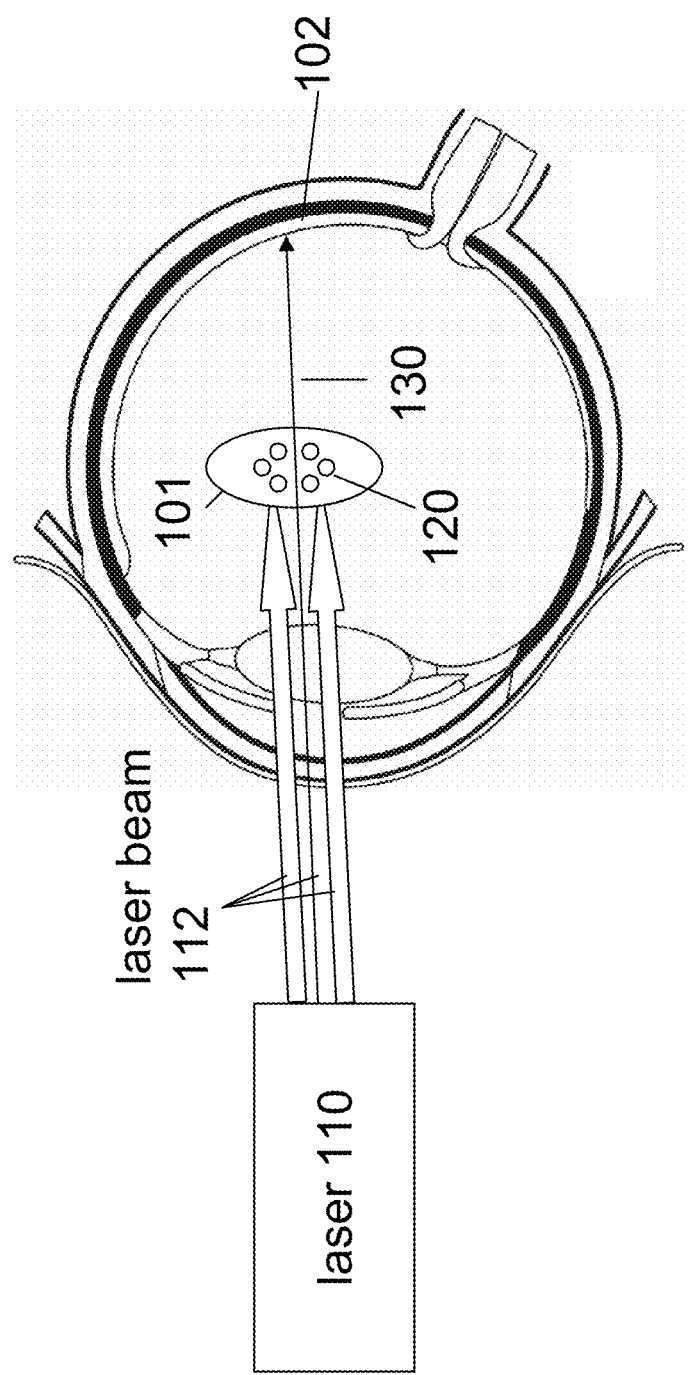
FIG. 2 illustrates an example of an ophthalmic surgical procedure without the introduction of a protection region.

FIG. 2 illustrates a laser photodisruptive process without the above described protection barrier being formed between the surgical target region and the retina. A pulsed laser 110 can be used to generate a laser beam 112, consisting of laser pulses. The laser beam 112 can be focused and directed to an ocular target 101 to perform a laser surgery. Photodisruption byproducts 120 may be created in the ocular target 101 as a result of the laser-induced photodisruption. Photodisruption byproducts 120 may include gas bubbles with size widely varying from below 1 micron to hundreds of microns, as well as tissue whose optical properties were altered by the laser beam 112. Residual light 130 that did not participate in the photodisruption of the ocular target 101 and was not absorbed by it, or which was scattered by the photodisruption byproduct 120 can reach the retina 102 and, if sufficiently powerful, can damage the retina 102.

Figure 3A:
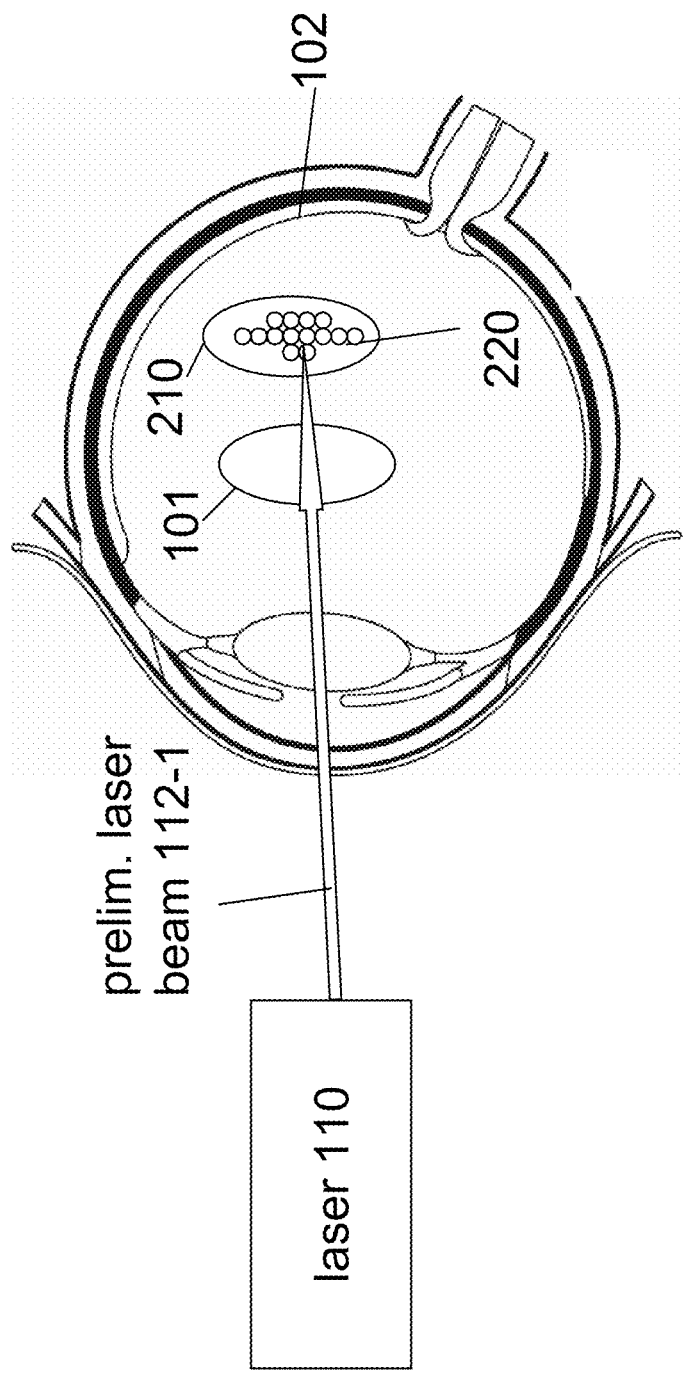
FIGS. 3A-B illustrate an example of an analogous ophthalmic surgical procedure with the introduction of a protection region.
Figure 3B:
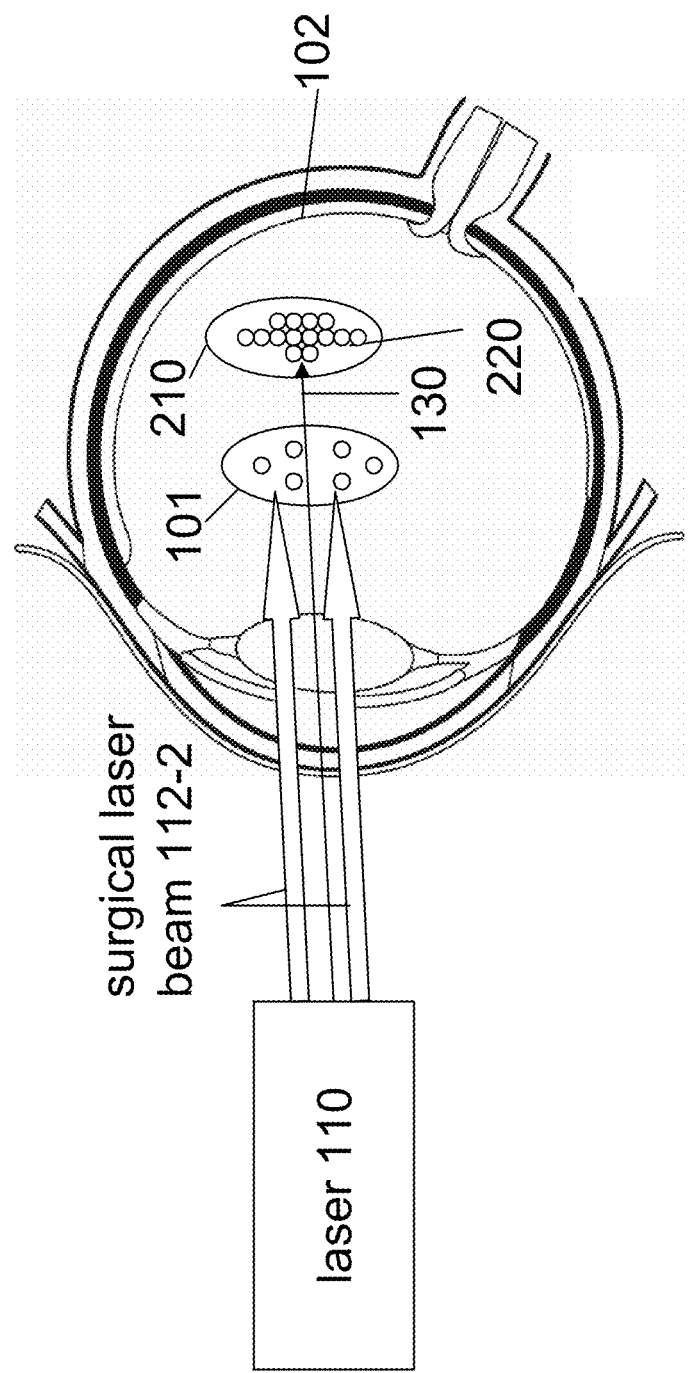

FIGS. 3A-B illustrate a laser photodisruptive process with the above described protection barrier being formed. In a preparatory step, a potential for retinal injury can be estimated based on the characteristics of a surgical laser system, on preparatory measurements and observations of the eye of the patient and the nature of the eye-problem, among other factors.

One or more damage-threshold laser parameters can be estimated within this preparatory step, representing the conditions when the laser beam 112 can cause damage to the retina 102 or another preselected photosensitive tissue. Laser parameters include an energy, pulse duration, spatial separation, and repetition rate of laser pulses.

Further, one or more protection-threshold laser parameters can be also estimated in this preparatory step, which represent the conditions when a laser beam can create photodisruption byproducts 120 in a preselected region, capable of protecting the retina 102 or another photosensitive tissue. The protection-threshold may depend on the tissue or region where the photodisruption byproduct 120 is to be generated.

FIG. 3A illustrates that prior to applying surgical laser pulses to the ocular target 101, the laser 110 can be operated and controlled to deliver preliminary photodisruptive laser pulses 112-1 to a selected protection region 210 between the retina 102 and a surgical target 101. The laser-parameters of the preliminary photodisruptive laser pulses 112-1 can be selected to be between the damage-threshold and the protection-threshold parameters estimated in the preparatory step. With such a choice, the preliminary laser pulses 112-1 are able to photodisrupt or optically alter a tissue in the protection region 210, while avoiding causing damage to the retina 102.

One result of the application of the preliminary laser pulses 112-1 can be the creation of a protection barrier 220 in the protection region 210, formed by photodisruption byproducts 120. Photodisruption byproducts 120 may include gas bubbles of various sizes, as well as tissue with altered optical properties, such as transparency or opacity. This protection barrier 220 may shield the retina 102, or other photosensitive tissue from subsequent application of surgical laser pulses 112-2, whose laser parameters may be beyond the damage-threshold.

Because the retina 102 is curved, the shape of the protection barrier 220 can be made to partially surround the ocular target region 101 as a barrier between the ocular target 101 and the retina 102. Such protection barriers 220 may be able to block the residual light of the surgical laser pulses 112-2.

FIG. 3B illustrates that after the protection barrier 220 is formed, the laser 110 may be operated to deliver high power surgical laser pulses 112-2 to the ocular target 101 to perform eye-surgery on the ocular target 101. Even though the laser parameters of the surgical laser pulses 112-2 may be beyond the damage-threshold, due to the blocking or scattering of the residual light 130 by the pre-formed protection barrier 220, the retina 102 remains protected by the surgical laser pulses 112-2.

FIG. 4 illustrates steps of an implementation of the above described ophthalmic surgery method 400.

Step 410 includes determining a surgical target region 101 in an eye. Further, surgical laser parameters may be chosen for surgical laser pulses for an ophthalmic surgery on the surgical target region so that the surgical laser pulses are sufficient to achieve the desired surgery, while having limited impact on the retina.

Step 420 includes identifying a protection region 210. The protection region 210 can be selected to be located between the surgical target region 101 and a photosensitive tissue, such as the retina 102.

Protection region 210 can be also selected to be in the proximity of, or even adjacent to the posterior-most portion of the surgical target region 101. The shape of the protection region 210 can be planar or curved, possibly tracking the surface of the retina 102.

Step 420 includes in some cases determining a portion of a boundary of a nucleus of the eye as detailed in relation to step 610 of FIG. 6 below.

Step 430 includes estimating a damage-threshold of the photosensitive tissue and a protection-threshold of the protection region of laser parameters in relation to the ophthalmic surgery. This step 430 may include analyzing the characteristics of elements of a surgical laser system, preparatory and pre-operative measurements, observations of the eye of the patient, using calculations, using an age-based algorithm, cadaver experiments, consulting data-bases and the nature of the eye-problem, among other factors.

One or more damage-threshold laser parameters can be estimated representing the conditions when the laser beam 112 can cause damage to the retina 102 or another photosensitive tissue. Laser parameters include an energy, pulse duration, spatial separation of pulses, repetition rate and the total number or duration of repetitions of laser pulses of the laser beam 112. The damage-threshold may depend on characteristics of the retina 102 or the photosensitive tissue.

Further, one or more protection-threshold laser parameters can be also estimated representing the conditions when a laser beam can create photodisruption byproducts 120 in the protection region, capable of protecting the retina 102 or another photosensitive tissue. Such byproducts may include gas bubbles or a tissue whose optical properties have been altered. These optical properties may include the transparency and opacity of a tissue or the gas bubbles. The protection-threshold may be selected so that the photodisruption byproducts 120, caused by a laser beam with these protection-threshold parameters are capable to block, deflect, scatter, absorb or in some other manner mitigate against the potential for retinal injury when the surgical pulses are applied. For example, the protection-threshold laser parameters may be chosen so that cavitation bubbles, generated by a laser beam with these protection-threshold parameters are generated with sufficient density that they are capable of blocking a laser beam with surgical parameters.

Identifying the protection region in step 420 and estimating the protection-threshold in step 430 may be performed iteratively. In an example, the operator of the laser 110 may choose an intended protection region 210, then perform a preparatory measurement on that region to estimate a protection-threshold, then find the protection-threshold undesirable, change the intended protection region 210 and newly estimate the protection-threshold.

Step 440 includes applying a set of preliminary laser pulses 112-1 focused at or near the identified protection region 210, wherein the laser parameters of the preliminary laser pulses 112-1 are between the damage-threshold and the protection-threshold. Step 440 may include applying the preliminary laser pulses 112-1 so as to form a protection barrier 220 in the protection region 210. The protection barrier 220 may include photodisruption byproducts 120, such as gas bubbles or tissue whose optical properties have been altered. The shape of the protection barrier 220 can be planar or curved, possibly tracking the surface of the retina 102.

The protection barrier 220 may include bubbles which are essentially permanent, or bubbles which are only temporary and eventually dissolve.

Step 450 includes applying surgical laser pulses 112-2 with surgical laser parameters possibly exceeding the damage threshold to the selected ocular target region 101.

As a result of the above described method 400, high repetition rate laser pulses can be delivered to ocular targets 101 at energies and repetition rates that are optimal for surgery on these targets but that otherwise would present a potential for retinal injury in the absence of the protection barrier 220 formed by the preliminary laser pulses 112-1. This technique can be especially beneficial when surgery is performed behind the natural protectors of the retina, such as the iris. Other examples include surgery performed on the lens or vitreous humor or structures in the vitreous cavity of the eye.

In an embodiment of method 400, the laser 110 is first controlled to deliver preliminary laser pulses 112-1 and is then controlled to deliver the surgical laser pulses 112-2. In one implementation of an ocular surgery using photodisruption, a laser 110 can be used to produce laser pulses capable of generating photodisruption at repetition rates of hundred pulses per second to billion pulses per second. An optics module can be used to focus and direct the laser pulses to ocular structures.

Laser pulse parameters can be selected for the application of one or more preliminary laser pulses 112-1 that do not present a risk for retinal injury. The one or more preliminary laser pulses 112-1 can be directed to a selected protection region 210 between the retina 102 and the desired surgical target 101, possibly even in the posterior portion of the surgical target 101 itself. The preliminary laser pulses 112-1 can generate photodisruption byproducts 120 within the protection region 210 to create the protection barrier 220.

After delivery of one or more preliminary laser pulses 112-1, surgical laser pulse parameters for one or more surgical laser pulses 112-2 that may present a risk for retinal injury can be selected. The surgical laser 110 and the optics module may be controlled to deliver the one or more surgical laser pulses 112-2 to the target 101 to perform the surgery. The photodisruption byproducts 120, generated by the preliminary laser pulses 112-1 may shield the retina 102 from the residual light 130 and other effects of the surgical laser pulses 112-2 during the surgery.

FIGS. 5-8 illustrate a specific implementation of the above method 400. This embodiment is related to performing a cataract surgery including treating the nucleus of the eye.

Figure 5:
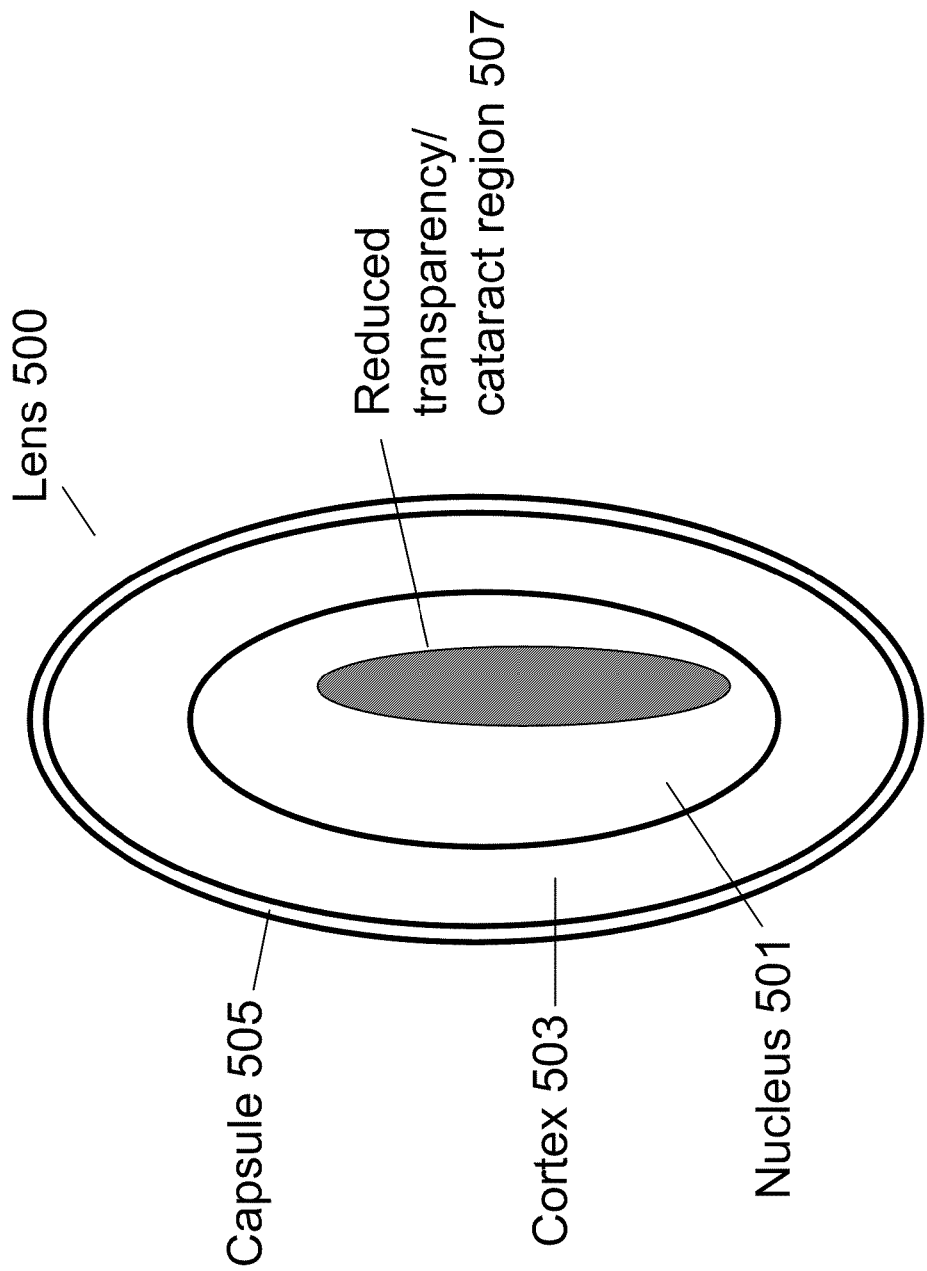
FIG. 5 illustrates the nucleus of an eye.

FIG. 5 illustrates that in a lens 500 of the human eye a region may develop a reduced transparency. The lens 500 is sometimes referred to as crystalline lens because of the $\alpha$, $\beta$, and $\gamma$ crystalline proteins, which make up about 90% of the lens. The crystalline lens has multiple optical functions in the eye, including its dynamic focusing capability. The lens is a unique tissue of the human body in that it continues to grow in size during gestation, after birth and throughout life. The lens grows by developing new lens fiber cells starting from the germinal center located on the equatorial periphery of the lens. The new growth around a nucleus 501, called a cortex 503, develops in concentric ellipsoid layers, regions, or zones. Because the nucleus 501 and the cortex 503 are formed at different stages of the human development, their optical properties are distinct.

As a result of this complex growth process, a typical lens 500 includes the harder nucleus 501 with an axial extent of about 2 mm, surrounded by the softer cortex 503 of axial width of 1-2 mm, contained by a much thinner capsule membrane 505, of typical width of about 20 microns. These values may change from person to person to a considerable degree.

Lens fiber cells undergo progressive loss of cytoplasmic elements with the passage of time. Since no blood veins or lymphatics reach the lens to supply its inner zone, with advancing age the optical clarity, flexibility and other functional properties of the lens sometimes deteriorate.

In some circumstances, including long-term ultraviolet exposure, exposure to radiation in general, denaturation of lens proteins, secondary effects of diseases such as diabetes, hypertension and advanced age, a region of the nucleus 501 can become a reduced transparency region 507. One result of such changes is the development of presbyopia and cataract that increase in severity and incidence with age.

The reduced transparency or cataract region 507 can be removed via a cataract surgery. A common procedure is to make an incision into the capsule 505 of the cloudy lens (capsulotomy), and surgically remove the interior, i.e. the cortex 503 and the nucleus 501, while leaving the lens capsule 505 essentially intact. While the cortex 503 exhibits viscous fluid dynamics and thus can be removed by aspiration or even simple suction, the nucleus is too hard for this approach. In previous procedures the nucleus 501 was typically removed as a whole. This procedure required making a rather large incision on the capsule 505, e.g. with a length of 12 mm. Finally, a plastic "intra-ocular" lens was often inserted into the capsule 505 as a replacement of the nucleus 501. However, such large scale intervention into such a sensitive organ often leads to unwanted consequences, e.g. making additional surgery necessary.

Cataract surgery can be performed efficiently by implementing the above described method 400. Implementations of the present application include photodisruptive methods to break up the nucleus 501 in order to facilitate its removal through a much smaller incision of the capsule 505. This may reduce the unintended secondary effects and can reduce the percentage of patients who need secondary cataract surgery.

In some embodiments the photodisruptive methods are applied to a hard lens region, which may differ to some extent from the nucleus 501. It may include only a portion of the nucleus 501 e.g. when the nucleus is to be sculpted instead of being removed. In other cases a region around the nucleus 501 may be also treated with photodisruptive methods. All variations of the hard lens region will be collectively referred to as the nucleus 501. In some cases this nucleus 501 may occupy an ellipsoid-like region of approximately 6-8 mm in equatorial diameter and approximately 2-3.5 mm in axial diameter, or extent. The size of this region may be different for different patients, for different disease and for different procedures.

In a laser-induced lens fragmentation process, laser pulses ionize and gasify the target region, leading to the formation of cavitation bubbles as photodisruptive byproducts 120. These bubbles may form with a diameter of a few microns and expand with supersonic speeds to 50-100 microns. As the expansion of the bubbles decelerates to subsonic speeds, they may induce shockwaves in the surrounding tissue, causing secondary disruption. Both the bubbles themselves and the induced shockwaves carry out a goal of the procedure: the disruption, fragmentation or emulsification of the targeted nucleus 501 without having made an incision on the capsule 505. The disrupted nucleus 501 can then be removed through a much smaller incision, possibly without inserting a surgical device into the lens itself.

However, the laser pulses in this procedure may have energy, pulse duration, spatial separation, repetition rate or another laser parameter which can cause damage to the retina 102.

The danger of the potential damage to the retina 102 can be reduced by applying lower energy pulses or reducing the repetition rates of the laser pulses. However, doing so also reduces the impact of the laser pulses 112 and this increases the time required to complete the eye surgery.

It is often the case that the time available for the surgery is limited, as the eye of the patient starts to move more and more uncontrollably for a variety of reasons. Typical surgery times are of the order of one minute and rarely exceed two minutes.

Applying the above described method 400 or its variants to first form a protection barrier 220 with preliminary laser pulses 112-1 affords the operator of the eye surgical laser 110 to apply subsequent surgical laser pulses 112-2 with greater energy and in higher density. Without the protection barrier 220 laser pulses with such surgical laser parameters would have damaged the retina 102. This method therefore can reduce the time needed for the surgery.

FIG. 6 illustrates an implementation of an eye-surgical process 600 to photodisrupt the nucleus 501 in relation to a cataract surgery, developed from the above considerations.

FIG. 7 illustrates an embodiment of the method of FIG. 6, wherein the photodisruption byproducts 120 are mainly gas bubbles. Other embodiments of the photodisruption byproducts 120 are also possible.

In step 610 a boundary 702 of the nucleus 501 can be determined from measuring a mechanical or optical characteristic of the lens 500. Implementations of the method 600 may include step 610 because if the laser pulses are applied outside the nucleus 501, the generated bubbles may expand considerably and in a hard-to-control manner. Therefore, some implementations may include first a determination of the boundary 702 of the nucleus 501 so that the preliminary laser pulses 112-1 can be focused inside the nucleus 501 in a protection region 210 to form a well-controlled protection barrier 220.

Figure 8:
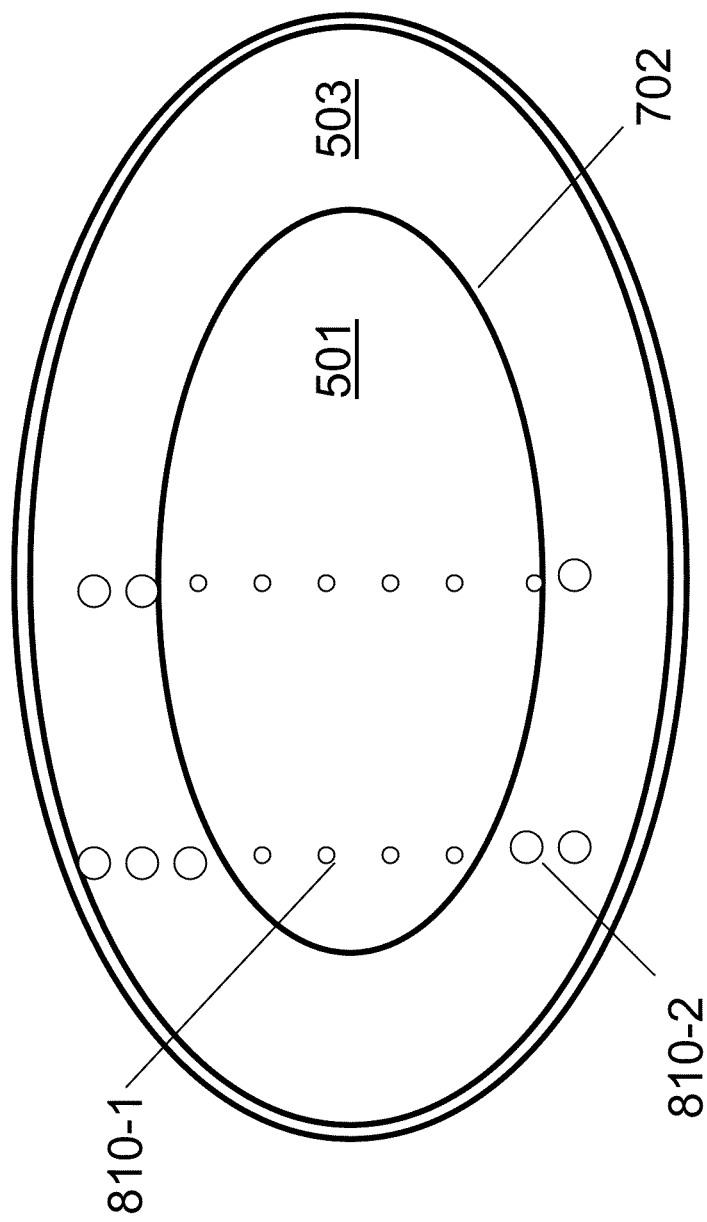
FIG. 8 illustrates an embodiment of step 610.

FIG. 8 shows an implementation of step 610 based on mechanical characteristics of the bubbles. A string of probe-bubbles 810 may be generated in the lens 500, for example, substantially parallel with a main axis of the eye, separated by a suitable distance, such as 10 to 100 microns. Other bubble strings can be generated at other areas of the lens. As shown, since the harder nucleus 501 shows more resistance against the bubble expansion than the soft cortex 503, the probe-bubbles 810-1 inside the hard nucleus 501 may expand slower than in the cortex 503. By the same token, the cortex 503 may exert less resistance against the expansion of the bubbles than the nucleus 501 and thus the probe-bubbles 810-2 in the cortex 503 may expand faster. A portion of the boundary 702 between the nucleus 501 and the cortex 503 can then be identified as the line or region separating slow-expanding probe-bubbles 810-1 from fast-expanding probe-bubbles 810-2.

The expansion of the probe-bubbles 810 and the identified separating line may be observed and tracked by an optical observation method. Many such methods are known, including all kinds of imaging techniques. Mapping out or otherwise recording these separation points can be used to establish the boundary 702, or at least a portion of it between the harder nucleus 501 and the softer cortex 503 lens regions. This implementation of step 610 can be pre-operative, i.e. performed prior to the surgical procedure or intra-operative, i.e. performed as an early phase of the surgical procedure.

Several other methods can be applied for step 610 as well. For example, optical or structural measurements can be performed prior to the surgical procedure on the patient. Or, some database can be used, which correlates some other measurable characteristic of the eye to the size of the nucleus, e.g. using an age-dependent algorithm. In some cases, an explicit calculation can be employed as well. In some cases even data from cadavers can be utilized. It is also possible to generate the above bubble string, then apply an ultrasound agitation, and observe the induced oscillation of the bubbles, especially their frequency. From these observations, the hardness of the surrounding tissue can be inferred as well.

In some cases the method of Optical Coherence Tomography (OCT) can be utilized in step 610. Among other aspects, OCT can measure the opacity of the imaged tissue. From this measurement, the size of the bubbles and the hardness of the region can be inferred once again.

In addition, the nucleus 501 can be selected based on some other consideration, e.g. when only the cataract region is to be removed, or the nucleus 501 is to be sculpted only. All of these methods are within the scope of step 610 of FIG. 6, and are illustrated in FIG. 7A with the dotted line indicating the boundary 702 of the nucleus 501.

FIG. 6 illustrates that in step 620 a damage-threshold of the retina 102 and a protection-threshold of the nucleus 501 can be determined. As described above in relation to step 430, the energy, spot separation, duration and repeat frequency of the preliminary laser pulses 112-1 can be selected based on a preoperative measurement of optical or structural properties of the lens. Alternatively, the selection of the laser energy and the target separation can be based on a preoperative measurement of the overall lens dimensions and the use of an age-dependant algorithm, calculations, cadaver measurements, databases, or any equivalent suitable method.

The thresholds can refer to any of the laser parameters. For example, in some implementations the duration of the preliminary laser pulses 112-1 may vary between the thresholds of 0.01 picoseconds and 50 picoseconds. In some implementations, the laser energy per preliminary laser pulse can vary between the thresholds of 0.5 microJ and 50 microJ. Some procedures may use an energy per pulse in the range of 5 microJ to 25 microJ. The laser pulse repetition rate can vary between the thresholds of 10 kHz and 100 MHz.

Step 630 includes applying preliminary laser pulses 112-1 with laser parameters between the determined thresholds to a protection region 210 in a posterior region of the nucleus 501 to form a protection barrier 220. The protection barrier 220 can include photodisruption byproducts 120 such as gas bubbles. Since the laser parameters of the preliminary laser pulses 112-1 are between the damage-threshold and the protection threshold, they do not damage the retina 102 in an appreciable manner, while they are capable of forming the protection barrier 220.

FIG. 7B illustrates an embodiment of step 630, where a protection region 210 is identified in a posterior region of the nucleus 501 in the proximity of the boundary 702, followed by applying the preliminary laser pulses 112-1 to form the protection barrier 220. The step 630 may include generating bubbles to photodisrupt, fragment, or even emulsify the tissue of the protection barrier 220 of the nucleus 501.

Step 640 includes applying surgical laser pulses 112-2 to a surgical target region 101 anterior to the protection barrier 220 in the nucleus 501. Since the protection barrier 220 has been formed in step 630, the laser parameters of the surgical laser pulses 112-2 may be selected to exceed the damage-threshold. Such laser pulses could have damaged the retina 102 without the protection barrier 220 formed in the preceding step 630.

FIG. 7C illustrates an embodiment of step 640, where a second set of bubbles are generated in the surgical target region 101 by surgical laser pulses 112-2. The surgical target region 101 can be anterior to the already formed protection barrier 220.

In both steps 630 and 640 the laser pulses 112 can be focused to a small region (e.g. with diameter of 1-10 microns) and then the focal point may be moved in a systematic manner, such as on a spiral or concentric path. In other implementations, the laser pulses 112 are applied to more extended regions, such as to a region with a diameter of hundreds of microns, in which case limited or no movement of the focal region may be needed.

In implementations of the method 600 the surgical step 640 can be repeatedly applied by moving the focal or target region of the surgical laser pulses 112-2 along a direction from the posterior of the nucleus 501 to the anterior of the nucleus 501. This sequence of the surgical steps 640 controls and limits the buildup and spread of bubbles in the optical path of the subsequent surgical laser pulses 112-2. These implementations allow the subsequent surgical laser pulses 112-2 to deliver their entire energy to the target area, allow for better control of the subsequent surgical laser pulses 112-2, as well as clearer imaging of the surgical area for the benefit of the person conducting the procedure.

These steps 610-640 may be followed by the removal of the fragmented, disrupted, emulsified or otherwise modified nucleus 501, if required or desired, such as in a cataract surgery. One method of removing the fragmented, disrupted, or otherwise modified nucleus 501 is to create one or more small openings, or incisions in the lens capsule 505, and then insert an aspiration probe to remove the fragmented material by aspiration. In other implementations, simple suction can extract the fragmented material, as well as the non-fragmented viscous material, such as the cortex, without inserting a probe into the capsule. In yet other embodiments mechanical, suction, ultrasonic, laser, heated fluid or other removal means may be used.

FIGS. 9-28 illustrate various laser ophthalmic surgery systems that can be used to implement the above described techniques and procedures.

One important aspect of laser surgical procedures is precise control and aiming of a laser beam, e.g., the beam position and beam focusing. Laser surgery systems can be designed to include laser control and aiming tools to precisely target laser pulses to a particular target inside the tissue. In various nanosecond photodisruptive laser surgical systems, such as the Nd:YAG laser systems, the required level of targeting precision is relatively low. This is in part because the laser energy used is relatively high and thus the affected tissue area is also relatively large, often covering an impacted area with a dimension in the hundreds of microns. The time between laser pulses in such systems tend to be long and manual controlled targeting is feasible and is commonly used. One example of such manual targeting mechanisms is a biomicroscope to visualize the target tissue in combination with a secondary laser source used as an aiming beam. The surgeon manually moves the focus of a laser focusing lens, usually with a joystick control, which is parfocal (with or without an offset) with their image through the microscope, so that the surgical beam or aiming beam is in best focus on the intended target.

Such techniques designed for use with low repetition rate laser surgical systems may be difficult to use with high repetition rate lasers operating at thousands of shots per second and relatively low energy per pulse. In surgical operations with high repetition rate lasers, much higher precision may be required due to the small effects of each single laser pulse and much higher positioning speed may be required due to the need to deliver thousands of pulses to new treatment areas very quickly.

Examples of high repetition rate pulsed lasers for laser surgical systems include pulsed lasers at a pulse repetition rate of thousands of shots per second or higher with relatively low energy per pulse. Such lasers use relatively low energy per pulse to localize the tissue effect caused by laser-induced photodisruption, e.g., the impacted tissue area by photodisruption on the order of microns or tens of microns. This localized tissue effect can improve the precision of the laser surgery and can be desirable in certain surgical procedures such as laser eye surgery. In one example of such surgery, placement of many hundred, thousands or millions of contiguous, nearly contiguous or pulses separated by known distances, can be used to achieve certain desired surgical effects, such as tissue incisions, separations or fragmentation.

Various surgical procedures using high repetition rate photodisruptive laser surgical systems with shorter laser pulse durations may require high precision in positioning each pulse in the target tissue under surgery both in an absolute position with respect to a target location on the target tissue and a relative position with respect to preceding pulses. For example, in some cases, laser pulses may be required to be delivered next to each other with an accuracy of a few microns within the time between pulses, which can be on the order of microseconds. Because the time between two sequential pulses is short and the precision requirement for the pulse alignment is high, manual targeting as used in low repetition rate pulsed laser systems may be no longer adequate or feasible.

One technique to facilitate and control precise, high speed positioning requirement for delivery of laser pulses into the tissue is attaching a applanation plate made of a transparent material such as a glass with a predefined contact surface to the tissue so that the contact surface of the applanation plate forms a well-defined optical interface with the tissue. This well-defined interface can facilitate transmission and focusing of laser light into the tissue to control or reduce optical aberrations or variations (such as due to specific eye optical properties or changes that occur with surface drying) that are most critical at the air-tissue interface, which in the eye is at the anterior surface of the cornea. Contact lenses can be designed for various applications and targets inside the eye and other tissues, including ones that are disposable or reusable. The contact glass or applanation plate on the surface of the target tissue can be used as a reference plate relative to which laser pulses are focused through the adjustment of focusing elements within the laser delivery system. This use of a contact glass or applanation plate provides better control of the optical qualities of the tissue surface and thus allow laser pulses to be accurately placed at a high speed at a desired location (interaction point) in the target tissue relative to the applanation reference plate with little optical distortion of the laser pulses.

One way for implementing an applanation plate on an eye is to use the applanation plate to provide a positional reference for delivering the laser pulses into a target tissue in the eye. This use of the applanation plate as a positional reference can be based on the known desired location of laser pulse focus in the target with sufficient accuracy prior to firing the laser pulses and that the relative positions of the reference plate and the individual internal tissue target must remain constant during laser firing. In addition, this method can require the focusing of the laser pulse to the desired location to be predictable and repeatable between eyes or in different regions within the same eye. In practical systems, it can be difficult to use the applanation plate as a positional reference to precisely localize laser pulses intraocularly because the above conditions may not be met in practical systems.

For example, if the crystalline lens is the surgical target, the precise distance from the reference plate on the surface of the eye to the target tends to vary due to the presence of collapsible structures, such as the cornea itself, the anterior chamber, and the iris. Not only is their considerable variability in the distance between the applanated cornea and the lens between individual eyes, but there can also be variation within the same eye depending on the specific surgical and applanation technique used by the surgeon. In addition, there can be movement of the targeted lens tissue relative to the applanated surface during the firing of the thousands of laser pulses required for achieving the surgical effect, further complicating the accurate delivery of pulses. In addition, structure within the eye may move due to the build-up of photodisruptive byproducts, such as cavitation bubbles. For example, laser pulses delivered to the crystalline lens can cause the lens capsule to bulge forward, requiring adjustment to target this tissue for subsequent placement of laser pulses. Furthermore, it can be difficult to use computer models and simulations to predict, with sufficient accuracy, the actual location of target tissues after the applanation plate is removed and to adjust placement of laser pulses to achieve the desired localization without applanation in part because of the highly variable nature of applanation effects, which can depend on factors particular to the individual cornea or eye, and the specific surgical and applanation technique used by a surgeon.

In addition to the physical effects of applanation that disproportionably affect the localization of internal tissue structures, in some surgical processes, it may be desirable for a targeting system to anticipate or account for nonlinear characteristics of photodisruption which can occur when using short pulse duration lasers. Photodisruption is a nonlinear optical process in the tissue material and can cause complications in beam alignment and beam targeting. For example, one of the nonlinear optical effects in the tissue material when interacting with laser pulses during the photodisruption is that the refractive index of the tissue material experienced by the laser pulses is no longer a constant but varies with the intensity of the light. Because the intensity of the light in the laser pulses varies spatially within the pulsed laser beam, along and across the propagation direction of the pulsed laser beam, the refractive index of the tissue material also varies spatially. One consequence of this nonlinear refractive index is self-focusing or self-defocusing in the tissue material that changes the actual focus of and shifts the position of the focus of the pulsed laser beam inside the tissue. Therefore, a precise alignment of the pulsed laser beam to each target tissue position in the target tissue may also need to account for the nonlinear optical effects of the tissue material on the laser beam. In addition, it may be necessary to adjust the energy in each pulse to deliver the same physical effect in different regions of the target due to different physical characteristics, such as hardness, or due to optical considerations such as absorption or scattering of laser pulse light traveling to a particular region. In such cases, the differences in non-linear focusing effects between pulses of different energy values can also affect the laser alignment and laser targeting of the surgical pulses.

Thus, in surgical procedures in which non superficial structures are targeted, the use of a superficial applanation plate based on a positional reference provided by the applanation plate may be insufficient to achieve precise laser pulse localization in internal tissue targets. The use of the applanation plate as the reference for guiding laser delivery may require measurements of the thickness and plate position of the applanation plate with high accuracy because the deviation from nominal is directly translated into a depth precision error. High precision applanation lenses can be costly, especially for single use disposable applanation plates.

The techniques, apparatus and systems described in this document can be implemented in ways that provide a targeting mechanism to deliver short laser pulses through an applanation plate to a desired localization inside the eye with precision and at a high speed without requiring the known desired location of laser pulse focus in the target with sufficient accuracy prior to firing the laser pulses and without requiring that the relative positions of the reference plate and the individual internal tissue target remain constant during laser firing. As such, the present techniques, apparatus and systems can be used for various surgical procedures where physical conditions of the target tissue under surgery tend to vary and are difficult to control and the dimension of the applanation lens tends to vary from one lens to another. The present techniques, apparatus and systems may also be used for other surgical targets where distortion or movement of the surgical target relative to the surface of the structure is present or non-linear optical effects make precise targeting problematic. Examples for such surgical targets different from the eye include the heart, deeper tissue in the skin and others.

The present techniques, apparatus and systems can be implemented in ways that maintain the benefits provided by an applanation plate, including, for example, control of the surface shape and hydration, as well as reductions in optical distortion, while providing for the precise localization of photodisruption to internal structures of the applanated surface. This can be accomplished through the use of an integrated imaging device to localize the target tissue relative to the focusing optics of the delivery system. The exact type of imaging device and method can vary and may depend on the specific nature of the target and the required level of precision.

An applanation lens may be implemented with another mechanism to fix the eye to prevent translational and rotational movement of the eye. Examples of such fixation devices include the use of a suction ring. Such fixation mechanism can also lead to unwanted distortion or movement of the surgical target. The present techniques, apparatus and systems can be implemented to provide, for high repetition rate laser surgical systems that utilize an applanation plate and/or fixation means for non-superficial surgical targets, a targeting mechanism to provide intraoperative imaging to monitor such distortion and movement of the surgical target.

Specific examples of laser surgical techniques, apparatus and systems are described below to use an optical imaging module to capture images of a target tissue to obtain positioning information of the target tissue, e.g., before and during a surgical procedure. Such obtained positioning information can be used to control the positioning and focusing of the surgical laser beam in the target tissue to provide accurate control of the placement of the surgical laser pulses in high repetition rate laser systems. In one implementation, during a surgical procedure, the images obtained by the optical imaging module can be used to dynamically control the position and focus of the surgical laser beam. In addition, lower energy and shot laser pulses tend to be sensitive to optical distortions, such a laser surgical system can implement an applanation plate with a flat or curved interface attaching to the target tissue to provide a controlled and stable optical interface between the target tissue and the surgical laser system and to mitigate and control optical aberrations at the tissue surface.

Figure 9:
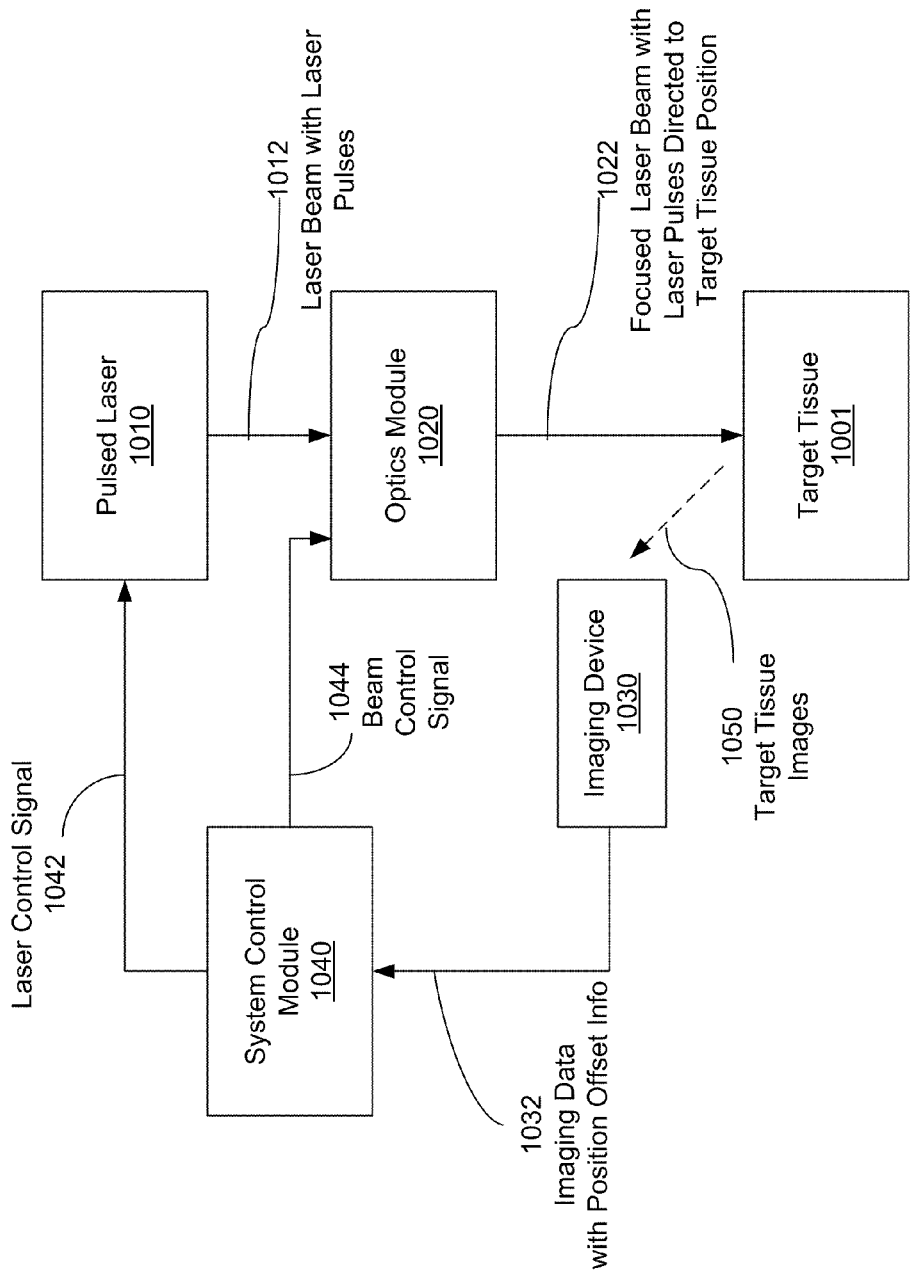
FIG. 9 shows an example of an imaging-guided laser surgical system in which an imaging module is provided to provide imaging of a target to the laser control.

As an example, FIG. 9 shows a laser surgical system based on optical imaging and applanation. This system includes a pulsed laser 1010 to produce a surgical laser beam 1012 of laser pulses, and an optics module 1020 to receive the surgical laser beam 1012 and to focus and direct the focused surgical laser beam 1022 onto a target tissue 1001, such as an eye, to cause photodisruption in the target tissue 1001. An applanation plate can be provided to be in contact with the target tissue 1001 to produce an interface for transmitting laser pulses to the target tissue 1001 and light coming from the target tissue 1001 through the interface. Notably, an optical imaging device 1030 is provided to capture light 1050 carrying target tissue images 1050 or imaging information from the target tissue 1001 to create an image of the target tissue 1001. The imaging signal 1032 from the imaging device 1030 is sent to a system control module 1040. The system control module 1040 operates to process the captured images from the image device 1030 and to control the optics module 1020 to adjust the position and focus of the surgical laser beam 1022 at the target tissue 101 based on information from the captured images. The optics module 120 can include one or more lenses and may further include one or more reflectors. A control actuator can be included in the optics module 1020 to adjust the focusing and the beam direction in response to a beam control signal 1044 from the system control module 1040. The control module 1040 can also control the pulsed laser 1010 via a laser control signal 1042.

The optical imaging device 1030 may be implemented to produce an optical imaging beam that is separate from the surgical laser beam 1022 to probe the target tissue 1001 and the returned light of the optical imaging beam is captured by the optical imaging device 1030 to obtain the images of the target tissue 1001. One example of such an optical imaging device 1030 is an optical coherence tomography (OCT) imaging module which uses two imaging beams, one probe beam directed to the target tissue 1001 thought the applanation plate and another reference beam in a reference optical path, to optically interfere with each other to obtain images of the target tissue 1001. In other implementations, the optical imaging device 1030 can use scattered or reflected light from the target tissue 1001 to capture images without sending a designated optical imaging beam to the target tissue 1001. For example, the imaging device 1030 can be a sensing array of sensing elements such as CCD or CMS sensors. For example, the images of photodisruption byproduct produced by the surgical laser beam 1022 may be captured by the optical imaging device 1030 for controlling the focusing and positioning of the surgical laser beam 1022. When the optical imaging device 1030 is designed to guide surgical laser beam alignment using the image of the photodisruption byproduct, the optical imaging device 1030 captures images of the photodisruption byproduct such as the laser-induced bubbles or cavities. The imaging device 1030 may also be an ultrasound imaging device to capture images based on acoustic images.

The system control module 1040 processes image data from the imaging device 1030 that includes the position offset information for the photodisruption byproduct from the target tissue position in the target tissue 1001. Based on the information obtained from the image, the beam control signal 1044 is generated to control the optics module 1020 which adjusts the laser beam 1022. A digital processing unit can be included in the system control module 1040 to perform various data processing for the laser alignment.

The above techniques and systems can be used deliver high repetition rate laser pulses to subsurface targets with a precision required for contiguous pulse placement, as needed for cutting or volume disruption applications. This can be accomplished with or without the use of a reference source on the surface of the target and can take into account movement of the target following applanation or during placement of laser pulses.

The applanation plate in the present systems is provided to facilitate and control precise, high speed positioning requirement for delivery of laser pulses into the tissue. Such an applanation plate can be made of a transparent material such as a glass with a predefined contact surface to the tissue so that the contact surface of the applanation plate forms a well-defined optical interface with the tissue. This well-defined interface can facilitate transmission and focusing of laser light into the tissue to control or reduce optical aberrations or variations (such as due to specific eye optical properties or changes that occur with surface drying) that are most critical at the air-tissue interface, which in the eye is at the anterior surface of the cornea. A number of contact lenses have been designed for various applications and targets inside the eye and other tissues, including ones that are disposable or reusable. The contact glass or applanation plate on the surface of the target tissue is used as a reference plate relative to which laser pulses are focused through the adjustment of focusing elements within the laser delivery system relative. Inherent in such an approach are the additional benefits afforded by the contact glass or applanation plate described previously, including control of the optical qualities of the tissue surface. Accordingly, laser pulses can be accurately placed at a high speed at a desired location (interaction point) in the target tissue relative to the applanation reference plate with little optical distortion of the laser pulses.

The optical imaging device 1030 in FIG. 9 captures images of the target tissue 1001 via the applanation plate. The control module 1040 processes the captured images to extract position information from the captured images and uses the extracted position information as a position reference or guide to control the position and focus of the surgical laser beam 1022. This imaging-guided laser surgery can be implemented without relying on the applanation plate as a position reference because the position of the applanation plate tends to change due to various factors as discussed above. Hence, although the applanation plate provides a desired optical interface for the surgical laser beam to enter the target tissue and to capture images of the target tissue, it may be difficult to use the applanation plate as a position reference to align and control the position and focus of the surgical laser beam for accurate delivery of laser pulses. The imaging-guided control of the position and focus of the surgical laser beam based on the imaging device 1030 and the control module 1040 allows the images of the target tissue 1001, e.g., images of inner structures of an eye, to be used as position references, without using the applanation plate to provide a position reference.

In addition to the physical effects of applanation that disproportionably affect the localization of internal tissue structures, in some surgical processes, it may be desirable for a targeting system to anticipate or account for nonlinear characteristics of photodisruption which can occur when using short pulse duration lasers. Photodisruption can cause complications in beam alignment and beam targeting. For example, one of the nonlinear optical effects in the tissue material when interacting with laser pulses during the photodisruption is that the refractive index of the tissue material experienced by the laser pulses is no longer a constant but varies with the intensity of the light. Because the intensity of the light in the laser pulses varies spatially within the pulsed laser beam, along and across the propagation direction of the pulsed laser beam, the refractive index of the tissue material also varies spatially. One consequence of this nonlinear refractive index is self-focusing or self-defocusing in the tissue material that changes the actual focus of and shifts the position of the focus of the pulsed laser beam inside the tissue. Therefore, a precise alignment of the pulsed laser beam to each target tissue position in the target tissue may also need to account for the nonlinear optical effects of the tissue material on the laser beam. The energy of the laser pulses may be adjusted to deliver the same physical effect in different regions of the target due to different physical characteristics, such as hardness, or due to optical considerations such as absorption or scattering of laser pulse light traveling to a particular region. In such cases, the differences in non-linear focusing effects between pulses of different energy values can also affect the laser alignment and laser targeting of the surgical pulses. In this regard, the direct images obtained from the target issue by the imaging device 1030 can be used to monitor the actual position of the surgical laser beam 1022 which reflects the combined effects of nonlinear optical effects in the target tissue and provide position references for control of the beam position and beam focus.

The techniques, apparatus and systems described here can be used in combination of an applanation plate to provide control of the surface shape and hydration, to reduce optical distortion, and provide for precise localization of photodisruption to internal structures through the applanated surface. The imaging-guided control of the beam position and focus described here can be applied to surgical systems and procedures that use means other than applanation plates to fix the eye, including the use of a suction ring which can lead to distortion or movement of the surgical target.

The following sections first describe examples of techniques, apparatus and systems for automated imaging-guided laser surgery based on varying degrees of integration of imaging functions into the laser control part of the systems. An optical or other modality imaging module, such as an OCT imaging module, can be used to direct a probe light or other type of beam to capture images of a target tissue, e.g., structures inside an eye. A surgical laser beam of laser pulses such as femtosecond or picosecond laser pulses can be guided by position information in the captured images to control the focusing and positioning of the surgical laser beam during the surgery. Both the surgical laser beam and the probe light beam can be sequentially or simultaneously directed to the target tissue during the surgery so that the surgical laser beam can be controlled based on the captured images to ensure precision and accuracy of the surgery.

Such imaging-guided laser surgery can be used to provide accurate and precise focusing and positioning of the surgical laser beam during the surgery because the beam control is based on images of the target tissue following applanation or fixation of the target tissue, either just before or nearly simultaneously with delivery of the surgical pulses. Notably, certain parameters of the target tissue such as the eye measured before the surgery may change during the surgery due to various factor such as preparation of the target tissue (e.g., fixating the eye to an applanation lens) and the alternation of the target tissue by the surgical operations. Therefore, measured parameters of the target tissue prior to such factors and/or the surgery may no longer reflect the physical conditions of the target tissue during the surgery. The present imaging-guided laser surgery can mitigate technical issues in connection with such changes for focusing and positioning the surgical laser beam before and during the surgery.

The present imaging-guided laser surgery may be effectively used for accurate surgical operations inside a target tissue. For example, when performing laser surgery inside the eye, laser light is focused inside the eye to achieve optical breakdown of the targeted tissue and such optical interactions can change the internal structure of the eye. For example, the crystalline lens can change its position, shape, thickness and diameter during accommodation, not only between prior measurement and surgery but also during surgery. Attaching the eye to the surgical instrument by mechanical means can change the shape of the eye in a not well defined way and further, the change can vary during surgery due to various factors, e.g., patient movement. Attaching means include fixating the eye with a suction ring and applanating the eye with a flat or curved lens. These changes amount to as much as a few millimeters. Mechanically referencing and fixating the surface of the eye such as the anterior surface of the cornea or limbus does not work well when performing precision laser microsurgery inside the eye.

The post preparation or near simultaneous imaging in the present imaging-guided laser surgery can be used to establish three-dimensional positional references between the inside features of the eye and the surgical instrument in an environment where changes occur prior to and during surgery. The positional reference information provided by the imaging prior to applanation and/or fixation of the eye, or during the actual surgery reflects the effects of changes in the eye and thus provides an accurate guidance to focusing and positioning of the surgical laser beam. A system based on the present imaging-guided laser surgery can be configured to be simple in structure and cost efficient. For example, a portion of the optical components associated with guiding the surgical laser beam can be shared with optical components for guiding the probe light beam for imaging the target tissue to simplify the device structure and the optical alignment and calibration of the imaging and surgical light beams.

The imaging-guided laser surgical systems described below use the OCT imaging as an example of an imaging instrument and other non-OCT imaging devices may also be used to capture images for controlling the surgical lasers during the surgery. As illustrated in the examples below, integration of the imaging and surgical subsystems can be implemented to various degrees. In the simplest form without integrating hardware, the imaging and laser surgical subsystems are separated and can communicate to one another through interfaces. Such designs can provide flexibility in the designs of the two subsystems. Integration between the two subsystems, by some hardware components such as a patient interface, further expands the functionality by offering better registration of surgical area to the hardware components, more accurate calibration and may improve workflow. As the degree of integration between the two subsystems increases, such a system may be made increasingly cost-efficient and compact and system calibration will be further simplified and more stable over time. Examples for imaging-guided laser systems in FIGS. 10-18 are integrated at various degrees of integration.

One implementation of a present imaging-guided laser surgical system, for example, includes a surgical laser that produces a surgical laser beam of surgical laser pulses that cause surgical changes in a target tissue under surgery; a patient interface mount that engages a patient interface in contact with the target tissue to hold the target tissue in position; and a laser beam delivery module located between the surgical laser and the patient interface and configured to direct the surgical laser beam to the target tissue through the patient interface. This laser beam delivery module is operable to scan the surgical laser beam in the target tissue along a predetermined surgical pattern. This system also includes a laser control module that controls operation of the surgical laser and controls the laser beam delivery module to produce the predetermined surgical pattern and an OCT module positioned relative to the patient interface to have a known spatial relation with respect to the patient interface and the target issue fixed to the patient interface. The OCT module is configured to direct an optical probe beam to the target tissue and receive returned probe light of the optical probe beam from the target tissue to capture OCT images of the target tissue while the surgical laser beam is being directed to the target tissue to perform an surgical operation so that the optical probe beam and the surgical laser beam are simultaneously present in the target tissue. The OCT module is in communication with the laser control module to send information of the captured OCT images to the laser control module.

In addition, the laser control module in this particular system responds to the information of the captured OCT images to operate the laser beam delivery module in focusing and scanning of the surgical laser beam and adjusts the focusing and scanning of the surgical laser beam in the target tissue based on positioning information in the captured OCT images.

In some implementations, acquiring a complete image of a target tissue may not be necessary for registering the target to the surgical instrument and it may be sufficient to acquire a portion of the target tissue, e.g., a few points from the surgical region such as natural or artificial landmarks. For example, a rigid body has 6 degrees of freedom in 3D space and six independent points would be sufficient to define the rigid body. When the exact size of the surgical region is not known, additional points are needed to provide the positional reference. In this regard, several points can be used to determine the position and the curvature of the anterior and posterior surfaces, which are normally different, and the thickness and diameter of the crystalline lens of the human eye. Based on these data a body made up from two halves of ellipsoid bodies with given parameters can approximate and visualize a crystalline lens for practical purposes. In another implementation, information from the captured image may be combined with information from other sources, such as pre-operative measurements of lens thickness that are used as an input for the controller.

Figure 10:
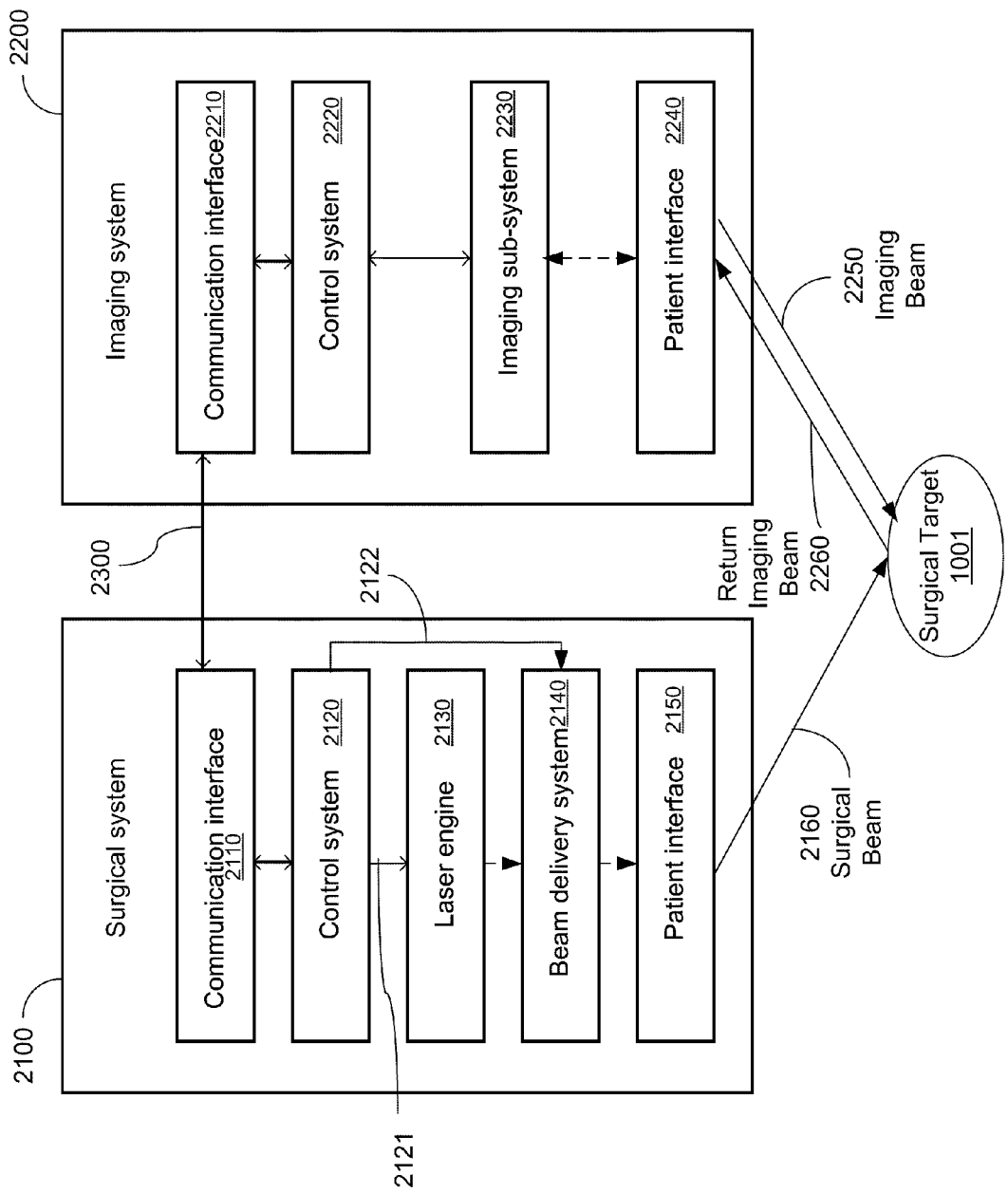
FIGS. 10-18 show examples of imaging-guided laser surgical systems with varying degrees of integration of a laser surgical system and an imaging system.

FIG. 10 shows one example of an imaging-guided laser surgical system with separated laser surgical system 2100 and imaging system 2200. The laser surgical system 2100 includes a laser engine 2130 with a surgical laser that produces a surgical laser beam 2160 of surgical laser pulses. A laser beam delivery module 2140 is provided to direct the surgical laser beam 2160 from the laser engine 2130 to the target tissue 1001 through a patient interface 2150 and is operable to scan the surgical laser beam 2160 in the target tissue 1001 along a predetermined surgical pattern. A laser control module 2120 is provided to control the operation of the surgical laser in the laser engine 2130 via a communication channel 2121 and controls the laser beam delivery module 2140 via a communication channel 2122 to produce the predetermined surgical pattern. A patient interface mount is provided to engage the patient interface 2150 in contact with the target tissue 1001 to hold the target tissue 1001 in position. The patient interface 2150 can be implemented to include a contact lens or applanation lens with a flat or curved surface to conformingly engage to the anterior surface of the eye and to hold the eye in position.

The imaging system 2200 in FIG. 10 can be an OCT module positioned relative to the patient interface 2150 of the surgical system 2100 to have a known spatial relation with respect to the patient interface 2150 and the target issue 1001 fixed to the patient interface 2150. This OCT module 2200 can be configured to have its own patient interface 2240 for interacting with the target tissue 1001. The imaging system 2200 includes an imaging control module 2220 and an imaging sub-system 2230. The sub-system 2230 includes a light source for generating imaging beam 2250 for imaging the target 1001 and an imaging beam delivery module to direct the optical probe beam or imaging beam 2250 to the target tissue 1001 and receive returned probe light 2260 of the optical imaging beam 2250 from the target tissue 1001 to capture OCT images of the target tissue 1001. Both the optical imaging beam 2250 and the surgical beam 2160 can be simultaneously directed to the target tissue 1001 to allow for sequential or simultaneous imaging and surgical operation.

As illustrated in FIG. 10, communication interfaces 2110 and 2210 are provided in both the laser surgical system 2100 and the imaging system 2200 to facilitate the communications between the laser control by the laser control module 2120 and imaging by the imaging system 2200 so that the OCT module 2200 can send information of the captured OCT images to the laser control module 2120. The laser control module 2120 in this system responds to the information of the captured OCT images to operate the laser beam delivery module 2140 in focusing and scanning of the surgical laser beam 2160 and dynamically adjusts the focusing and scanning of the surgical laser beam 2160 in the target tissue 1001 based on positioning information in the captured OCT images. The integration between the laser surgical system 2100 and the imaging system 2200 is mainly through communication between the communication interfaces 2110 and 2210 at the software level.

In this and other examples, various subsystems or devices may also be integrated. For example, certain diagnostic instruments such as wavefront aberrometers, corneal topography measuring devices may be provided in the system, or pre-operative information from these devices can be utilized to augment intra-operative imaging.

Figure 11:
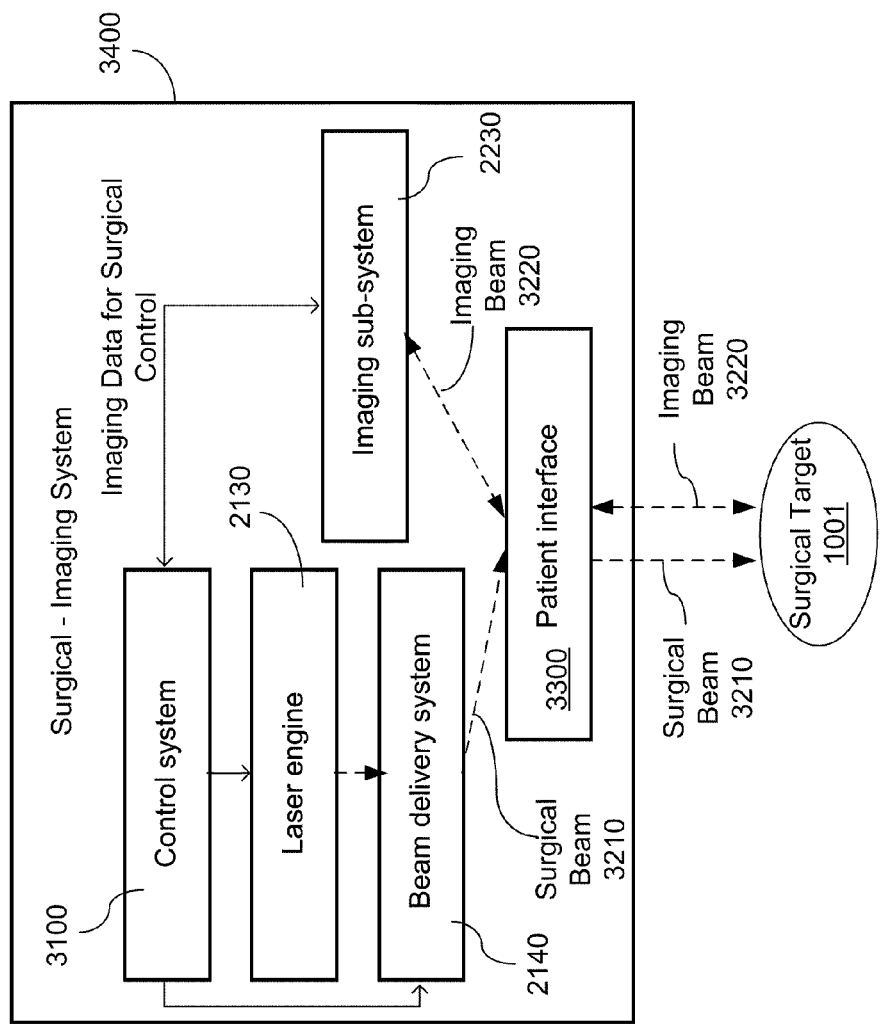

FIG. 11 shows an example of an imaging-guided laser surgical system with additional integration features. The imaging and surgical systems share a common patient interface 3300 which immobilizes target tissue 1001 (e.g., the eye) without having two separate patient interfaces as in FIG. 10. The surgical beam 3210 and the imaging beam 3220 are combined at the patient interface 3300 and are directed to the target 1001 by the common patient interface 3300. In addition, a common control module 3100 is provided to control both the imaging sub-system 2230 and the surgical part (the laser engine 2130 and the beam delivery system 2140). This increased integration between imaging and surgical parts allows accurate calibration of the two subsystems and the stability of the position of the patient and surgical volume. A common housing 3400 is provided to enclose both the surgical and imaging subsystems. When the two systems are not integrated into a common housing, the common patient interface 3300 can be part of either the imaging or the surgical subsystem.

Figure 12:
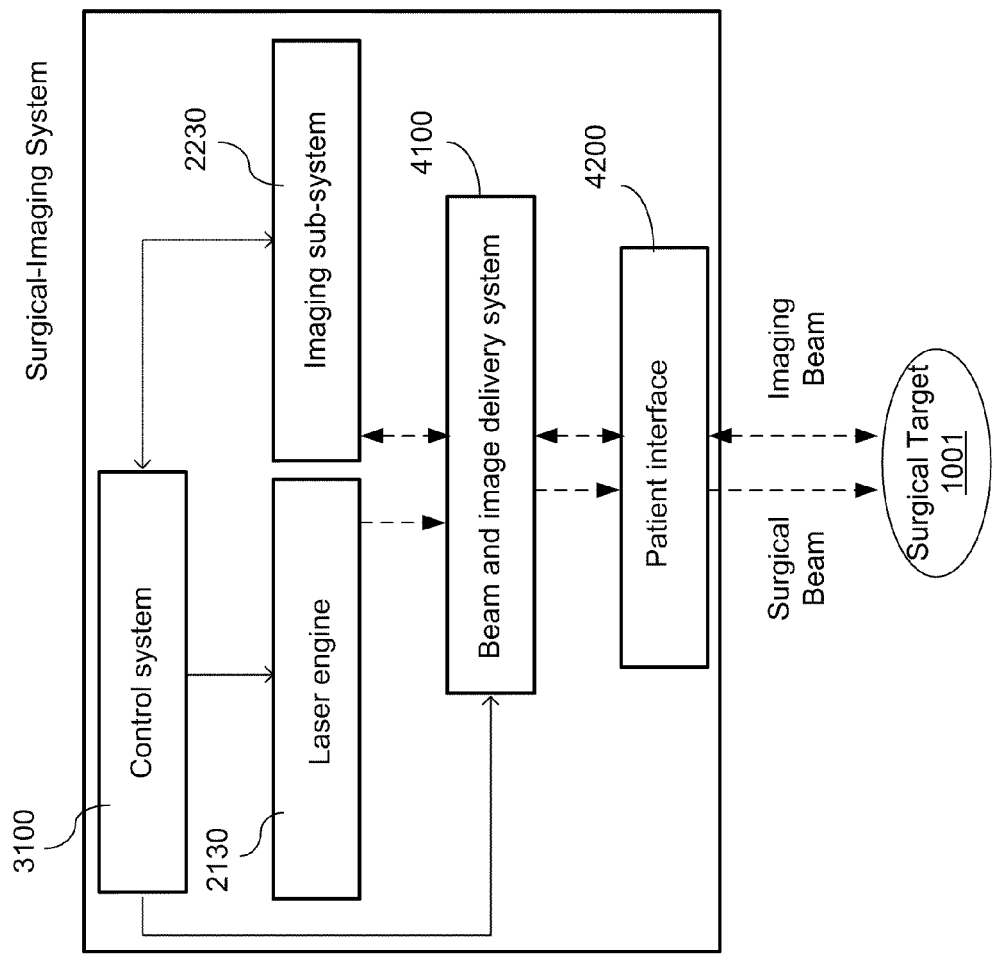

FIG. 12 shows an example of an imaging-guided laser surgical system where the laser surgical system and the imaging system share both a common beam delivery module 4100 and a common patient interface 4200. This integration further simplifies the system structure and system control operation.

In one implementation, the imaging system in the above and other examples can be an optical computed tomography (OCT) system and the laser surgical system is a femtosecond or picosecond laser based ophthalmic surgical system. In OCT, light from a low coherence, broadband light source such as a super luminescent diode is split into separate reference and signal beams. The signal beam is the imaging beam sent to the surgical target and the returned light of the imaging beam is collected and recombined coherently with the reference beam to form an interferometer. Scanning the signal beam perpendicularly to the optical axis of the optical train or the propagation direction of the light provides spatial resolution in the x-y direction while depth resolution comes from extracting differences between the path lengths of the reference arm and the returned signal beam in the signal arm of the interferometer. While the x-y scanner of different OCT implementations are essentially the same, comparing the path lengths and getting z-scan information can happen in different ways. In one implementation known as the time domain OCT, for example, the reference arm is continuously varied to change its path length while a photodetector detects interference modulation in the intensity of the re-combined beam. In a different implementation, the reference arm is essentially static and the spectrum of the combined light is analyzed for interference. The Fourier transform of the spectrum of the combined beam provides spatial information on the scattering from the interior of the sample. This method is known as the spectral domain or Fourier OCT method. In a different implementation known as a frequency swept OCT (S. R. Chinn, et. al. Opt. Lett. 22 (1997), a narrowband light source is used with its frequency swept rapidly across a spectral range. Interference between the reference and signal arms is detected by a fast detector and dynamic signal analyzer. An external cavity tuned diode laser or frequency tuned of frequency domain mode-locked (FDML) laser developed for this purpose (R. Huber et. al. Opt. Express, 13, 2005) (S. H. Yun, IEEE J. of Sel. Q. El. 3(4) p. 1087-1096, 1997) can be used in these examples as a light source. A femtosecond laser used as a light source in an OCT system can have sufficient bandwidth and can provide additional benefits of increased signal to noise ratios.

The OCT imaging device in the systems in this document can be used to perform various imaging functions. For example, the OCT can be used to suppress complex conjugates resulting from the optical configuration of the system or the presence of the applanation plate, capture OCT images of selected locations inside the target tissue to provide three-dimensional positioning information for controlling focusing and scanning of the surgical laser beam inside the target tissue, or capture OCT images of selected locations on the surface of the target tissue or on the applanation plate to provide positioning registration for controlling changes in orientation that occur with positional changes of the target, such as from upright to supine. The OCT can be calibrated by a positioning registration process based on placement of marks or markers in one positional orientation of the target that can then be detected by the OCT module when the target is in another positional orientation. In other implementations, the OCT imaging system can be used to produce a probe light beam that is polarized to optically gather the information on the internal structure of the eye. The laser beam and the probe light beam may be polarized in different polarizations. The OCT can include a polarization control mechanism that controls the probe light used for said optical tomography to polarize in one polarization when traveling toward the eye and in a different polarization when traveling away from the eye. The polarization control mechanism can include, e.g., a wave-plate or a Faraday rotator.

The system in FIG. 12 is shown as a spectral OCT configuration and can be configured to share the focusing optics part of the beam delivery module between the surgical and the imaging systems. The main requirements for the optics are related to the operating wavelength, image quality, resolution, distortion etc. The laser surgical system can be a femtosecond laser system with a high numerical aperture system designed to achieve diffraction limited focal spot sizes, e.g., about 2 to 3 micrometers. Various femtosecond ophthalmic surgical lasers can operate at various wavelengths such as wavelengths of around 1.05 micrometer. The operating wavelength of the imaging device can be selected to be close to the laser wavelength so that the optics is chromatically compensated for both wavelengths. Such a system may include a third optical channel, a visual observation channel such as a surgical microscope, to provide an additional imaging device to capture images of the target tissue. If the optical path for this third optical channel shares optics with the surgical laser beam and the light of the OCT imaging device, the shared optics can be configured with chromatic compensation in the visible spectral band for the third optical channel and the spectral bands for the surgical laser beam and the OCT imaging beam.

Figure 13:
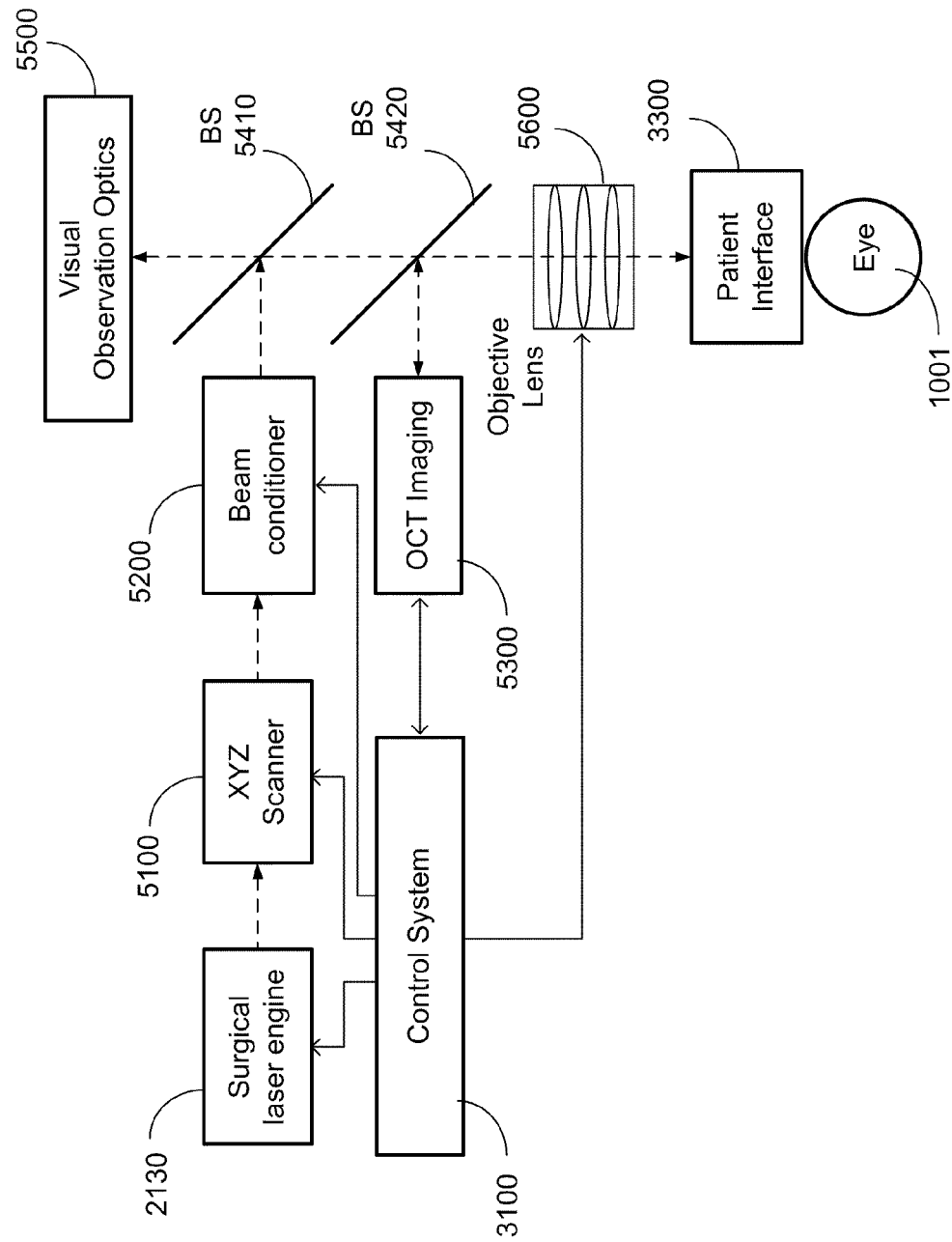

FIG. 13 shows a particular example of the design in FIG. 11 where the scanner 5100 for scanning the surgical laser beam and the beam conditioner 5200 for conditioning (collimating and focusing) the surgical laser beam are separate from the optics in the OCT imaging module 5300 for controlling the imaging beam for the OCT. The surgical and imaging systems share an objective lens 5600 module and the patient interface 3300. The objective lens 5600 directs and focuses both the surgical laser beam and the imaging beam to the patient interface 3300 and its focusing is controlled by the control module 3100. Two beam splitters 5410 and 5420 are provided to direct the surgical and imaging beams. The beam splitter 5420 is also used to direct the returned imaging beam back into the OCT imaging module 5300. Two beam splitters 5410 and 5420 also direct light from the target 1001 to a visual observation optics unit 5500 to provide direct view or image of the target 1001. The unit 5500 can be a lens imaging system for the surgeon to view the target 1001 or a camera to capture the image or video of the target 1001. Various beam splitters can be used, such as dichroic and polarization beam splitters, optical grating, holographic beam splitter or a combinations of these.

In some implementations, the optical components may be appropriately coated with antireflection coating for both the surgical and for the OCT wavelength to reduce glare from multiple surfaces of the optical beam path. Reflections would otherwise reduce the throughput of the system and reduce the signal to noise ratio by increasing background light in the OCT imaging unit. One way to reduce glare in the OCT is to rotate the polarization of the return light from the sample by wave-plate of Faraday isolator placed close to the target tissue and orient a polarizer in front of the OCT detector to preferentially detect light returned from the sample and suppress light scattered from the optical components.

In a laser surgical system, each of the surgical laser and the OCT system can have a beam scanner to cover the same surgical region in the target tissue. Hence, the beam scanning for the surgical laser beam and the beam scanning for the imaging beam can be integrated to share common scanning devices.

Figure 14:
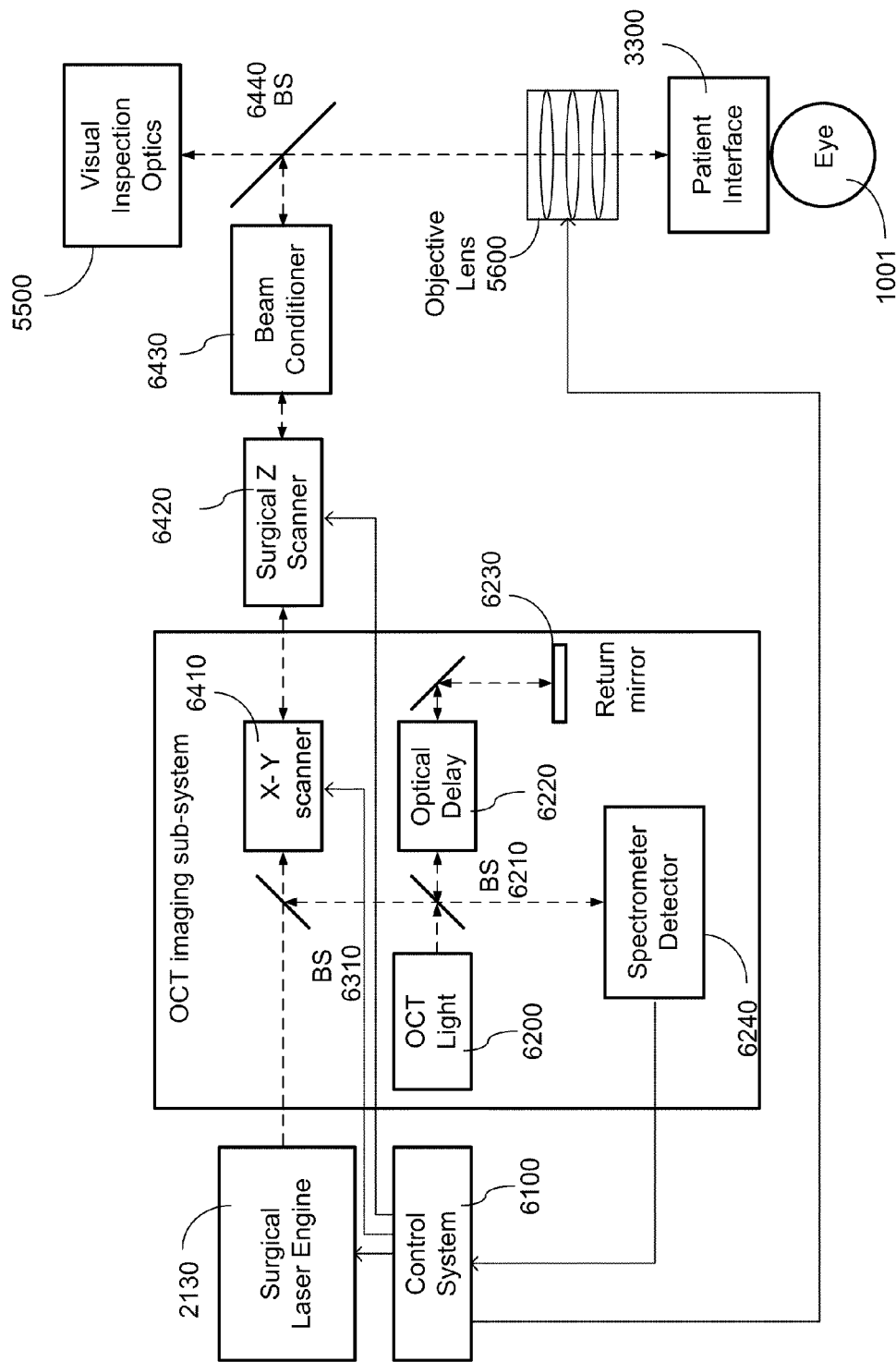

FIG. 14 shows an example of such a system in detail. In this implementation the x-y scanner 6410 and the z scanner 6420 are shared by both subsystems. A common control 6100 is provided to control the system operations for both surgical and imaging operations. The OCT sub-system includes an OCT light source 6200 that produces the imaging light that is split into an imaging beam and a reference beam by a beam splitter 6210. The imaging beam is combined with the surgical beam at the beam splitter 6310 to propagate along a common optical path leading to the target 1001. The scanners 6410 and 6420 and the beam conditioner unit 6430 are located downstream from the beam splitter 6310. A beam splitter 6440 is used to direct the imaging and surgical beams to the objective lens 5600 and the patient interface 3300.

In the OCT sub-system, the reference beam transmits through the beam splitter 6210 to an optical delay device 6220 and is reflected by a return mirror 6230. The returned imaging beam from the target 1001 is directed back to the beam splitter 6310 which reflects at least a portion of the returned imaging beam to the beam splitter 6210 where the reflected reference beam and the returned imaging beam overlap and interfere with each other. A spectrometer detector 6240 is used to detect the interference and to produce OCT images of the target 1001. The OCT image information is sent to the control system 6100 for controlling the surgical laser engine 2130, the scanners 6410 and 6420 and the objective lens 5600 to control the surgical laser beam. In one implementation, the optical delay device 6220 can be varied to change the optical delay to detect various depths in the target tissue 1001.

If the OCT system is a time domain system, the two sub-systems use two different z-scanners because the two scanners operate in different ways. In this example, the z scanner of the surgical system operates by changing the divergence of the surgical beam in the beam conditioner unit without changing the path lengths of the beam in the surgical beam path. On the other hand, the time domain OCT scans the z-direction by physically changing the beam path by a variable delay or by moving the position of the reference beam return mirror. After calibration, the two z-scanners can be synchronized by the laser control module. The relationship between the two movements can be simplified to a linear or polynomial dependence, which the control module can handle or alternatively calibration points can define a look-up table to provide proper scaling. Spectral/Fourier domain and frequency swept source OCT devices have no z-scanner, the length of the reference arm is static. Besides reducing costs, cross calibration of the two systems will be relatively straightforward. There is no need to compensate for differences arising from image distortions in the focusing optics or from the differences of the scanners of the two systems since they are shared.

In practical implementations of the surgical systems, the focusing objective lens 5600 is slidably or movably mounted on a base and the weight of the objective lens is balanced to limit the force on the patient's eye. The patient interface 3300 can include an applanation lens attached to a patient interface mount. The patient interface mount is attached to a mounting unit, which holds the focusing objective lens. This mounting unit is designed to ensure a stable connection between the patient interface and the system in case of unavoidable movement of the patient and allows gentler docking of the patient interface onto the eye. Various implementations for the focusing objective lens can be used. This presence of an adjustable focusing objective lens can change the optical path length of the optical probe light as part of the optical interferometer for the OCT sub-system. Movement of the objective lens 5600 and patient interface 3300 can change the path length differences between the reference beam and the imaging signal beam of the OCT in an uncontrolled way and this may degrade the OCT depth information detected by the OCT. This would happen not only in time-domain but also in spectral/Fourier domain and frequency-swept OCT systems.

Figure 15:
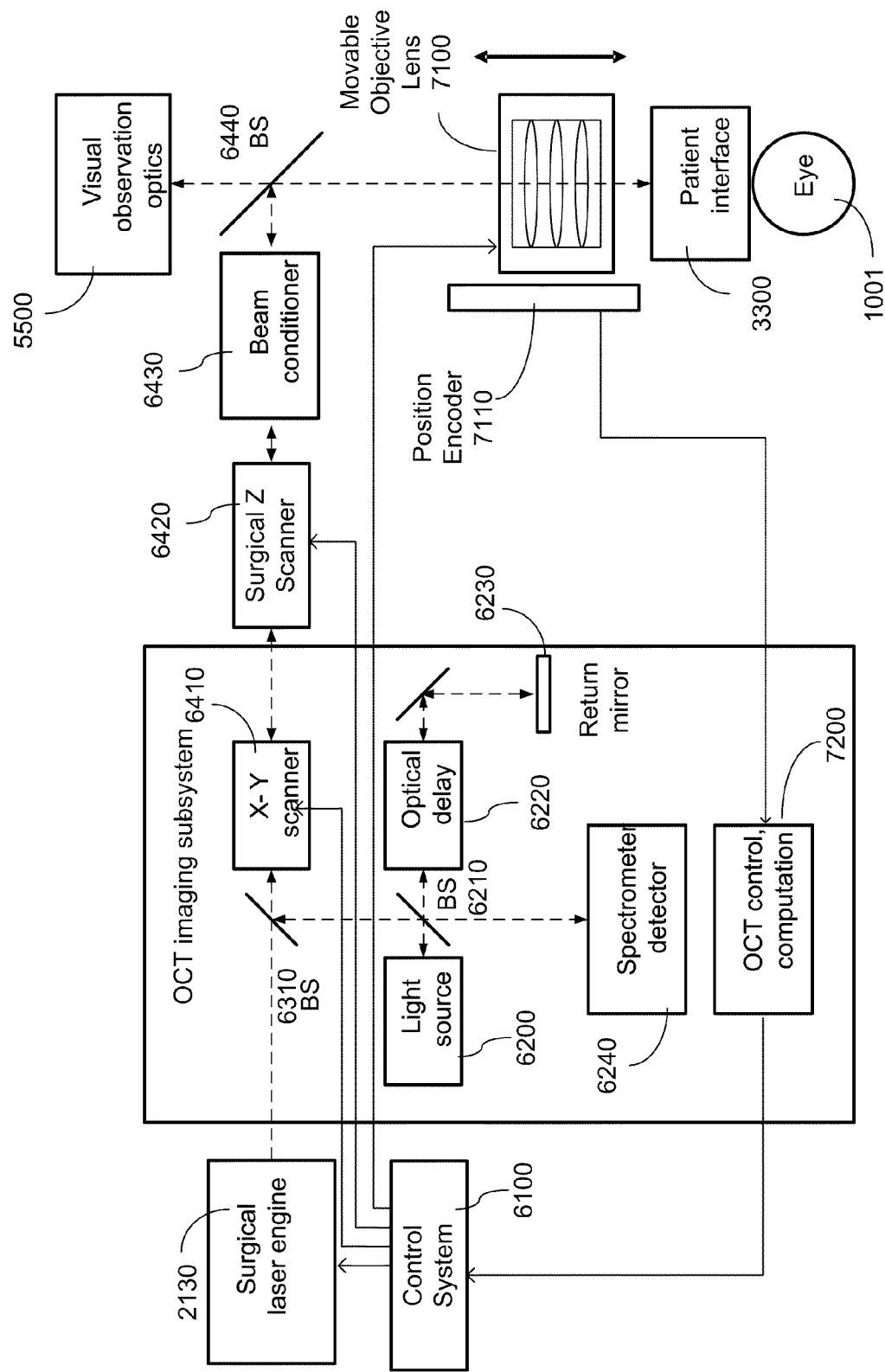
Figure 16:
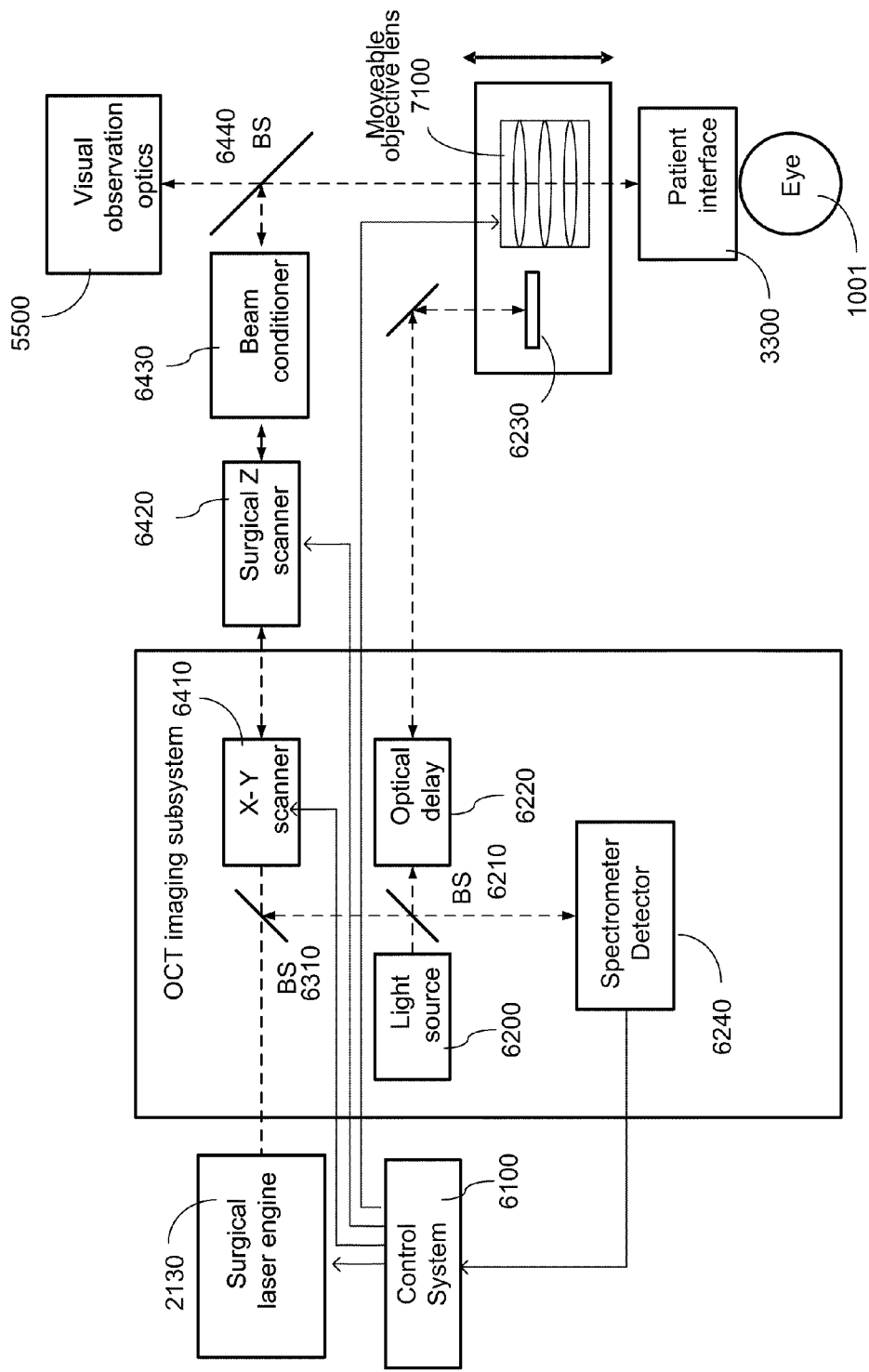

FIGS. 15 and 16 show exemplary imaging-guided laser surgical systems that address the technical issue associated with the adjustable focusing objective lens.

The system in FIG. 15 provides a position sensing device 7110 coupled to the movable focusing objective lens 7100 to measure the position of the objective lens 7100 on a slideable mount and communicates the measured position to a control module 7200 in the OCT system. The control system 6100 can control and move the position of the objective lens 7100 to adjust the optical path length traveled by the imaging signal beam for the OCT operation and the position of the lens 7100 is measured and monitored by the position encoder 7110 and direct fed to the OCT control 7200. The control module 7200 in the OCT system applies an algorithm, when assembling a 3D image in processing the OCT data, to compensate for differences between the reference arm and the signal arm of the interferometer inside the OCT caused by the movement of the focusing objective lens 7100 relative to the patient interface 3300. The proper amount of the change in the position of the lens 7100 computed by the OCT control module 7200 is sent to the control 6100 which controls the lens 7100 to change its position.

FIG. 16 shows another exemplary system where the return mirror 6230 in the reference arm of the interferometer of the OCT system or at least one part in an optical path length delay assembly of the OCT system is rigidly attached to the movable focusing objective lens 7100 so the signal arm and the reference arm undergo the same amount of change in the optical path length when the objective lens 7100 moves. As such, the movement of the objective lens 7100 on the slide is automatically compensated for path-length differences in the OCT system without additional need for a computational compensation.

The above examples for imaging-guided laser surgical systems, the laser surgical system and the OCT system use different light sources. In an even more complete integration between the laser surgical system and the OCT system, a femtosecond surgical laser as a light source for the surgical laser beam can also be used as the light source for the OCT system.

Figure 17:
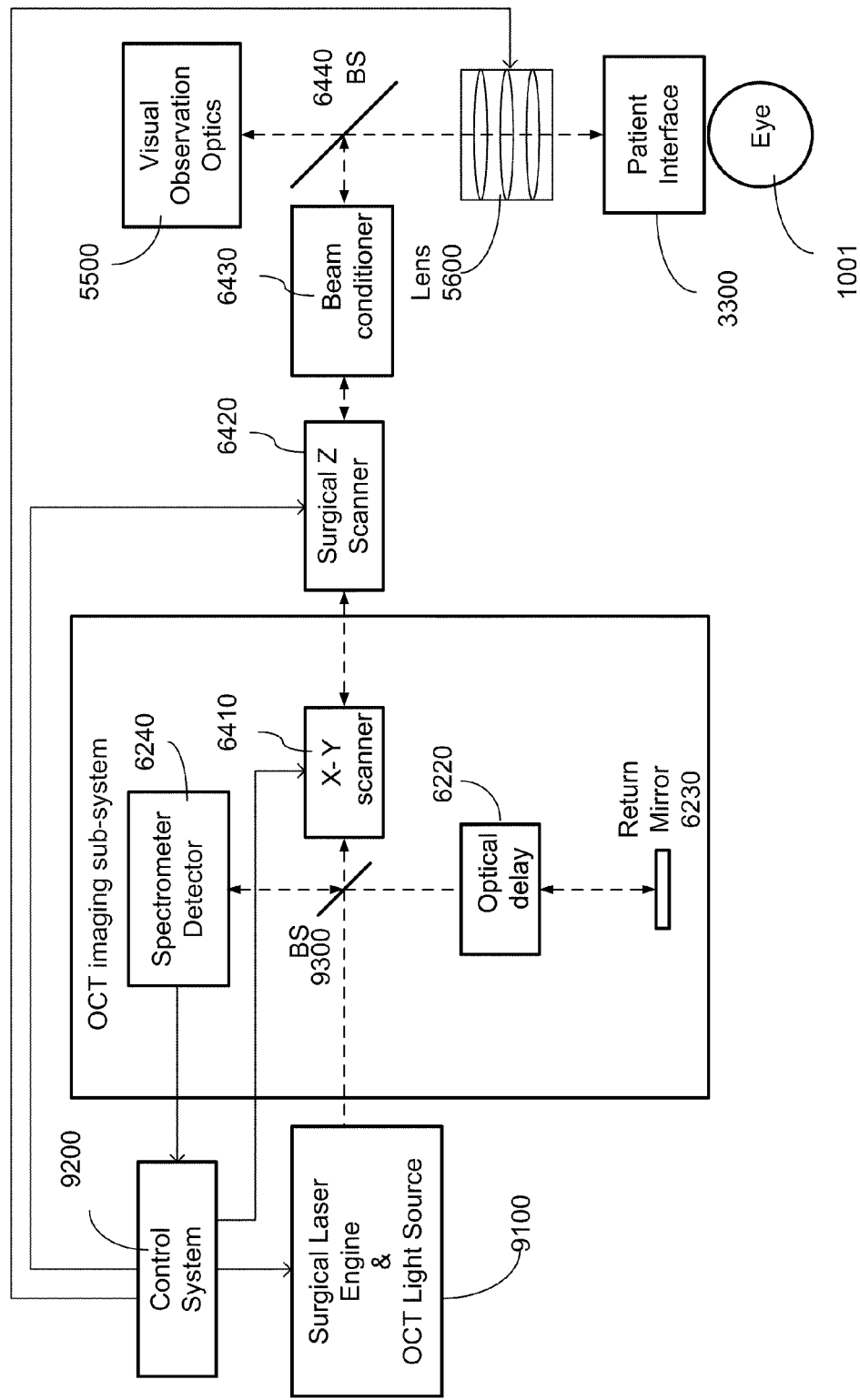

FIG. 17 shows an example where a femtosecond pulse laser in a light module 9100 is used to generate both the surgical laser beam for surgical operations and the probe light beam for OCT imaging. A beam splitter 9300 is provided to split the laser beam into a first beam as both the surgical laser beam and the signal beam for the OCT and a second beam as the reference beam for the OCT. The first beam is directed through an x-y scanner 6410 which scans the beam in the x and y directions perpendicular to the propagation direction of the first beam and a second scanner (z scanner) 6420 that changes the divergence of the beam to adjust the focusing of the first beam at the target tissue 1001. This first beam performs the surgical operations at the target tissue 1001 and a portion of this first beam is back scattered to the patient interface and is collected by the objective lens as the signal beam for the signal arm of the optical interferometer of the OCT system. This returned light is combined with the second beam that is reflected by a return mirror 6230 in the reference arm and is delayed by an adjustable optical delay element 6220 for a time-domain OCT to control the path difference between the signal and reference beams in imaging different depths of the target tissue 1001. The control system 9200 controls the system operations.

Surgical practice on the cornea has shown that a pulse duration of several hundred femtoseconds may be sufficient to achieve good surgical performance, while for OCT of a sufficient depth resolution broader spectral bandwidth generated by shorter pulses, e.g., below several tens of femtoseconds, are needed. In this context, the design of the OCT device dictates the duration of the pulses from the femtosecond surgical laser.

Figure 18:
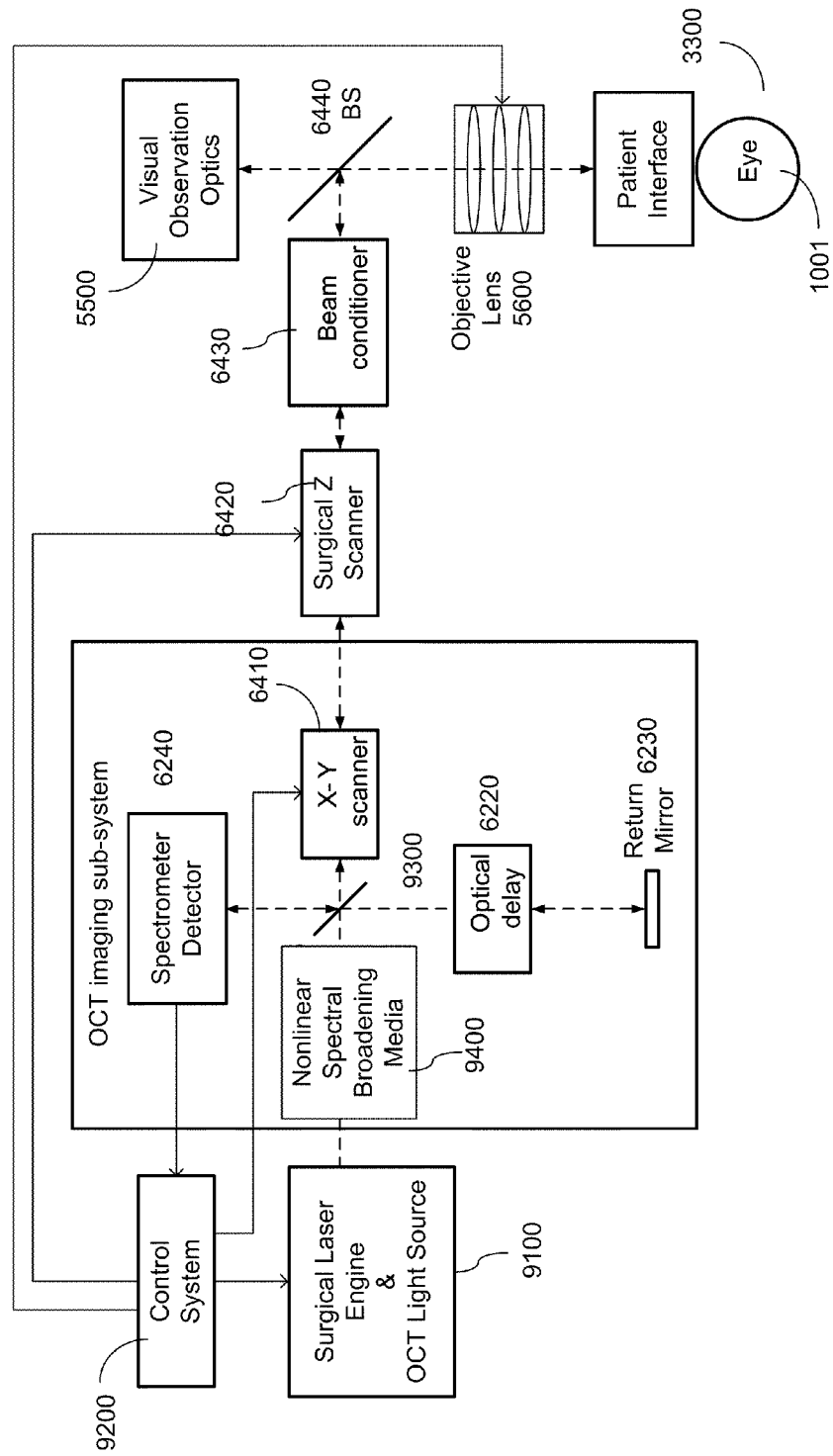

FIG. 18 shows another imaging-guided system that uses a single pulsed laser 9100 to produce the surgical light and the imaging light. A nonlinear spectral broadening media 9400 is placed in the output optical path of the femtosecond pulsed laser to use an optical non-linear process such as white light generation or spectral broadening to broaden the spectral bandwidth of the pulses from a laser source of relatively longer pulses, several hundred femtoseconds normally used in surgery. The media 9400 can be a fiber-optic material, for example. The light intensity requirements of the two systems are different and a mechanism to adjust beam intensities can be implemented to meet such requirements in the two systems. For example, beam steering mirrors, beam shutters or attenuators can be provided in the optical paths of the two systems to properly control the presence and intensity of the beam when taking an OCT image or performing surgery in order to protect the patient and sensitive instruments from excessive light intensity.

Figure 19:
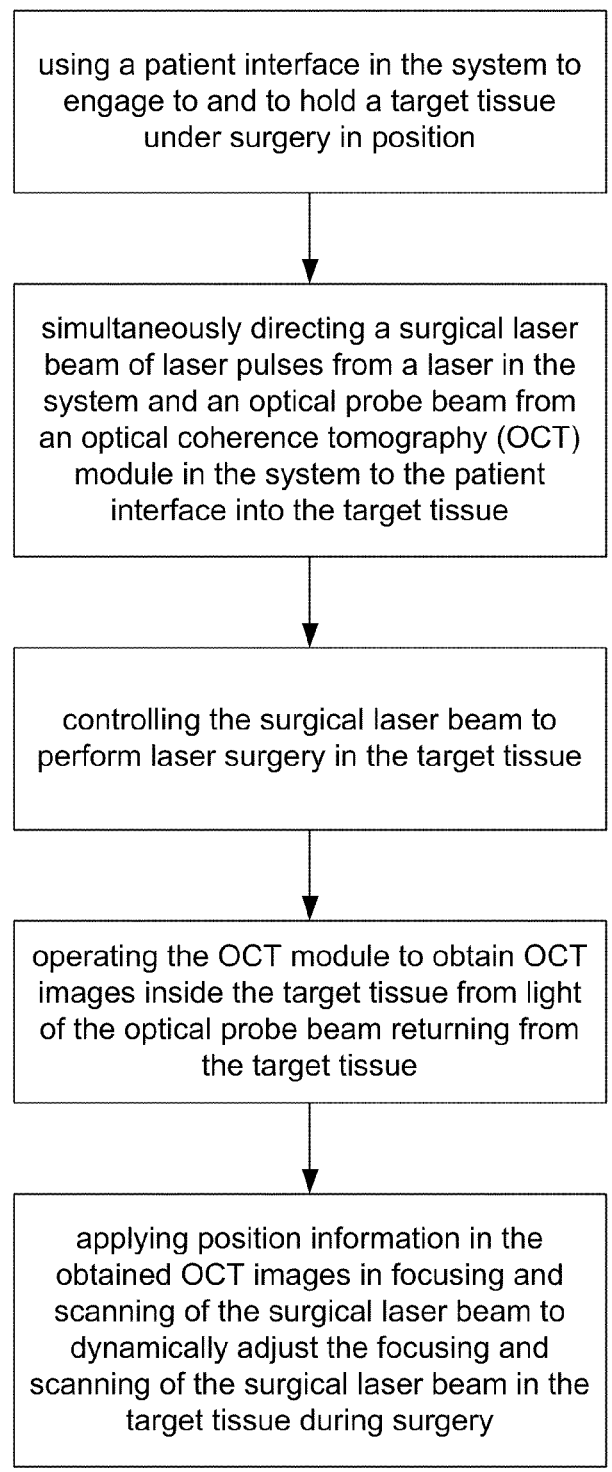
FIG. 19 shows an example of a method for performing laser surgery by suing an imaging-guided laser surgical system.

In operation, the above examples in FIGS. 10-18 can be used to perform imaging-guided laser surgery. FIG. 19 shows one example of a method for performing laser surgery by using an imaging-guided laser surgical system. This method uses a patient interface in the system to engage to and to hold a target tissue under surgery in position and simultaneously directs a surgical laser beam of laser pulses from a laser in the system and an optical probe beam from the OCT module in the system to the patient interface into the target tissue. The surgical laser beam is controlled to perform laser surgery in the target tissue and the OCT module is operated to obtain OCT images inside the target tissue from light of the optical probe beam returning from the target tissue. The position information in the obtained OCT images is applied in focusing and scanning of the surgical laser beam to adjust the focusing and scanning of the surgical laser beam in the target tissue before or during surgery.

Figure 20:
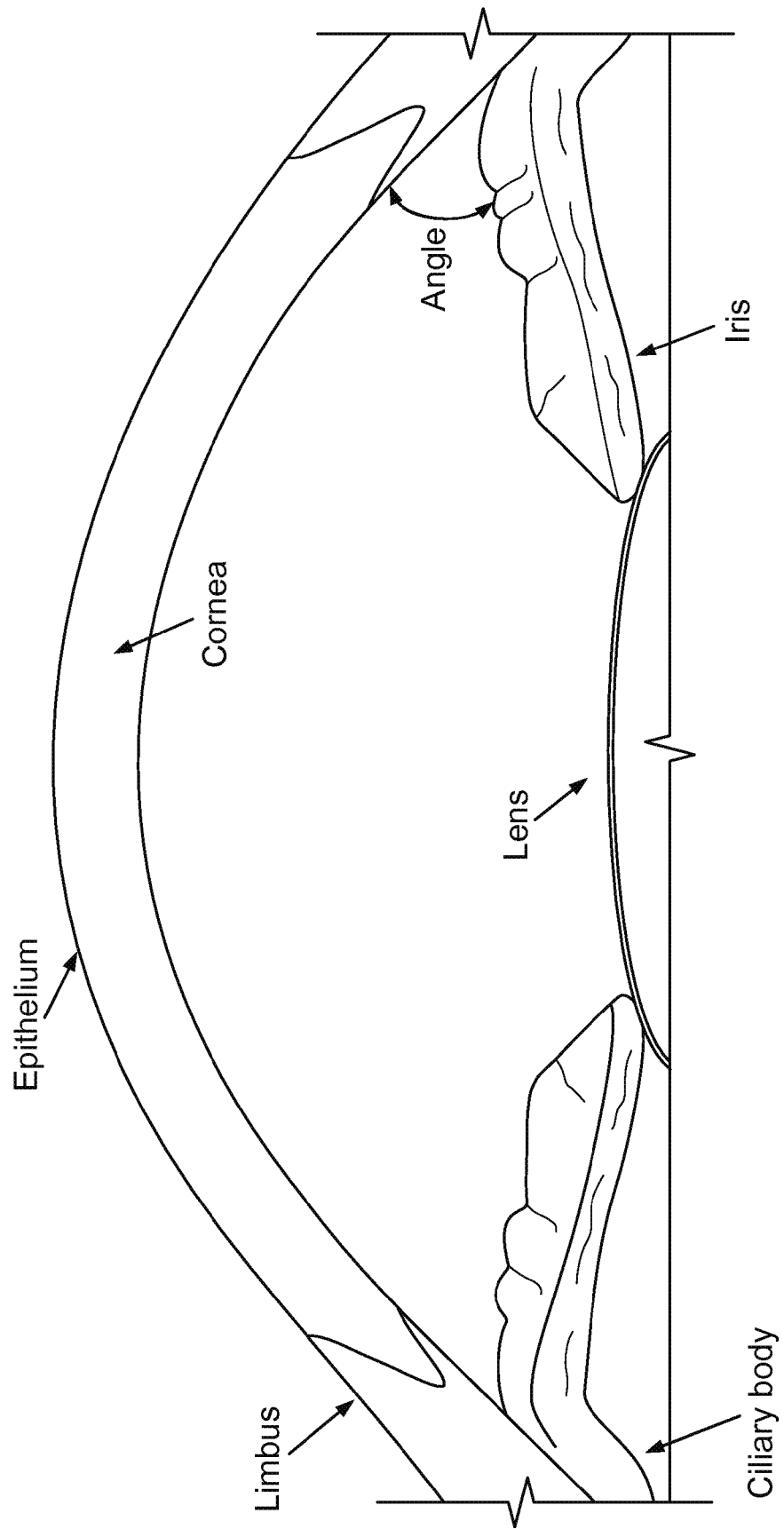
FIG. 20 shows an example of an image of an eye from an optical coherence tomography (OCT) imaging module.
Figure 21:
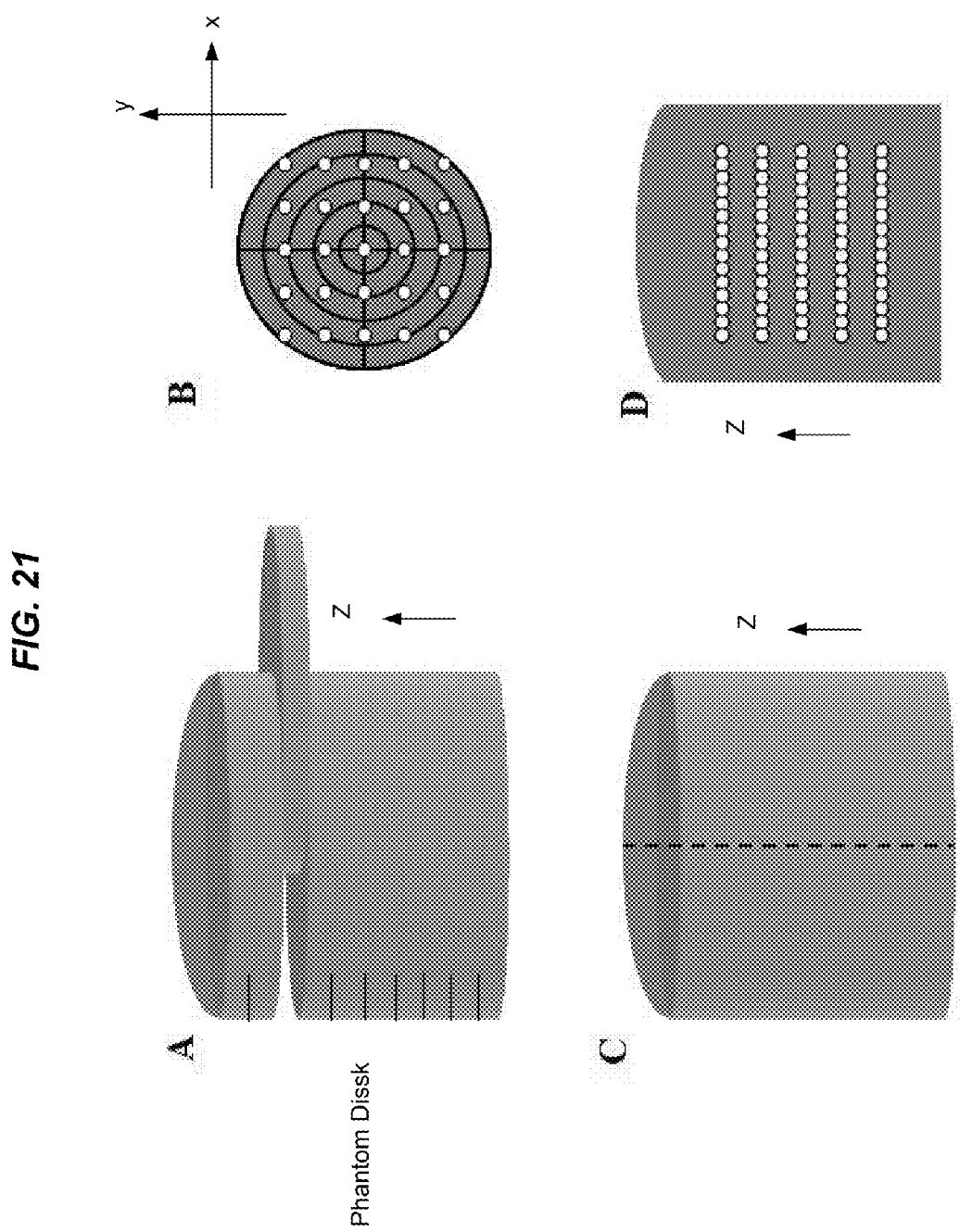
FIGS. 21A, 21B, 21C and 21D show two examples of calibration samples for calibrating an imaging-guided laser surgical system.

FIG. 20 shows an example of an OCT image of an eye. The contacting surface of the applanation lens in the patient interface can be configured to have a curvature that minimizes distortions or folds in the cornea due to the pressure exerted on the eye during applanation. After the eye is successfully applanated at the patient interface, an OCT image can be obtained. As illustrated in FIG. 20, the curvature of the lens and cornea as well as the distances between the lens and cornea are identifiable in the OCT image. Subtler features such as the epithelium-cornea interface are detectable. Each of these identifiable features may be used as an internal reference of the laser coordinates with the eye. The coordinates of the cornea and lens can be digitized using well-established computer vision algorithms such as Edge or Blob detection. Once the coordinates of the lens are established, they can be used to control the focusing and positioning of the surgical laser beam for the surgery.

Alternatively, a calibration sample material may be used to form a 3-D array of reference marks at locations with known position coordinates. The OCT image of the calibration sample material can be obtained to establish a mapping relationship between the known position coordinates of the reference marks and the OCT images of the reference marks in the obtained OCT image. This mapping relationship is stored as digital calibration data and is applied in controlling the focusing and scanning of the surgical laser beam during the surgery in the target tissue based on the OCT images of the target tissue obtained during the surgery. The OCT imaging system is used here as an example and this calibration can be applied to images obtained via other imaging techniques.

In an imaging-guided laser surgical system described here, the surgical laser can produce relatively high peak powers sufficient to drive strong field/multi-photon ionization inside of the eye (i.e. inside of the cornea and lens) under high numerical aperture focusing. Under these conditions, one pulse from the surgical laser generates a plasma within the focal volume. Cooling of the plasma results in a well defined damage zone or "bubble" that may be used as a reference point. The following sections describe a calibration procedure for calibrating the surgical laser against an OCT-based imaging system using the damage zones created by the surgical laser.

Before surgery can be performed, the OCT is calibrated against the surgical laser to establish a relative positioning relationship so that the surgical laser can be controlled in position at the target tissue with respect to the position associated with images in the OCT image of the target tissue obtained by the OCT. One way for performing this calibration uses a pre-calibrated target or "phantom" which can be damaged by the laser as well as imaged with the OCT. The phantom can be fabricated from various materials such as a glass or hard plastic (e.g. PMMA) such that the material can permanently record optical damage created by the surgical laser. The phantom can also be selected to have optical or other properties (such as water content) that are similar to the surgical target.

The phantom can be, e.g., a cylindrical material having a diameter of at least 10 mm (or that of the scanning range of the delivery system) and a cylindrical length of at least 10 mm long spanning the distance of the epithelium to the crystalline lens of the eye, or as long as the scanning depth of the surgical system. The upper surface of the phantom can be curved to mate seamlessly with the patient interface or the phantom material may be compressible to allow full applanation. The phantom may have a three dimensional grid such that both the laser position (in x and y) and focus (z), as well as the OCT image can be referenced against the phantom.

FIG. 21A-21D illustrate two exemplary configurations for the phantom. FIG. 21A illustrates a phantom that is segmented into thin disks. FIG. 21B shows a single disk patterned to have a grid of reference marks as a reference for determining the laser position across the phantom (i.e. the x- and y-coordinates). The z-coordinate (depth) can be determined by removing an individual disk from the stack and imaging it under a confocal microscope.

FIG. 21C illustrates a phantom that can be separated into two halves. Similar to the segmented phantom in FIG. 21A, this phantom is structured to contain a grid of reference marks as a reference for determining the laser position in the x- and y-coordinates. Depth information can be extracted by separating the phantom into the two halves and measuring the distance between damage zones. The combined information can provide the parameters for image guided surgery.

Figure 22:
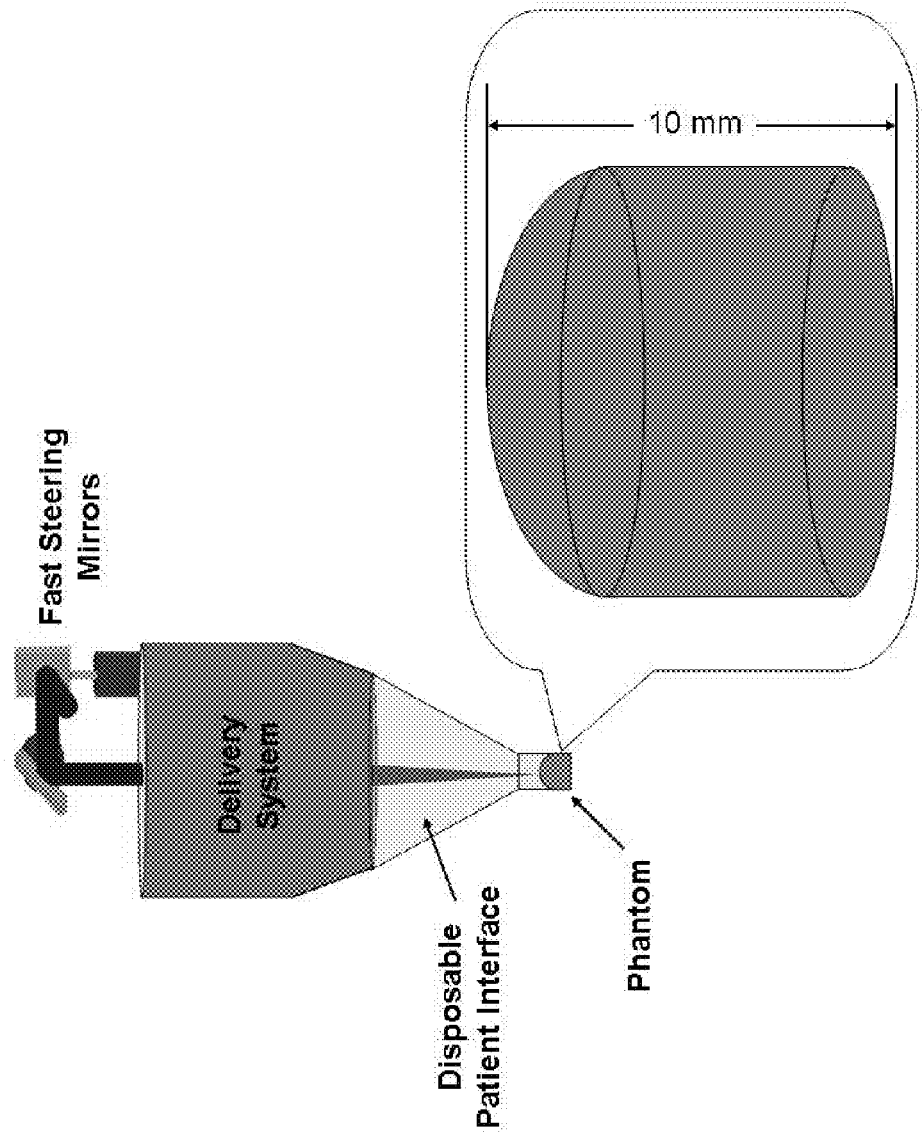
FIG. 22 shows an example of attaching a calibration sample material to a patient interface in an imaging-guided laser surgical system for calibrating the system.

FIG. 22 shows a surgical system part of the imaging-guided laser surgical system. This system includes steering mirrors which may be actuated by actuators such as galvanometers or voice coils, an objective lens e and a disposable patient interface. The surgical laser beam is reflected from the steering mirrors through the objective lens. The objective lens focuses the beam just after the patient interface. Scanning in the x- and y-coordinates is performed by changing the angle of the beam relative to the objective lens. Scanning in z-plane is accomplished by changing the divergence of the incoming beam using a system of lens upstream to the steering mirrors.

In this example, the conical section of the disposable patient interface may be either air spaced or solid and the section interfacing with the patient includes a curved contact lens. The curved contact lens can be fabricated from fused silica or other material resistant to forming color centers when irradiated with ionizing radiation. The radius of curvature is on the upper limit of what is compatible with the eye, e.g., about 10 mm.

The first step in the calibration procedure is docking the patient interface with the phantom. The curvature of the phantom matches the curvature of the patient interface. After docking, the next step in the procedure involves creating optical damage inside of the phantom to produce the reference marks.

Figure 23:
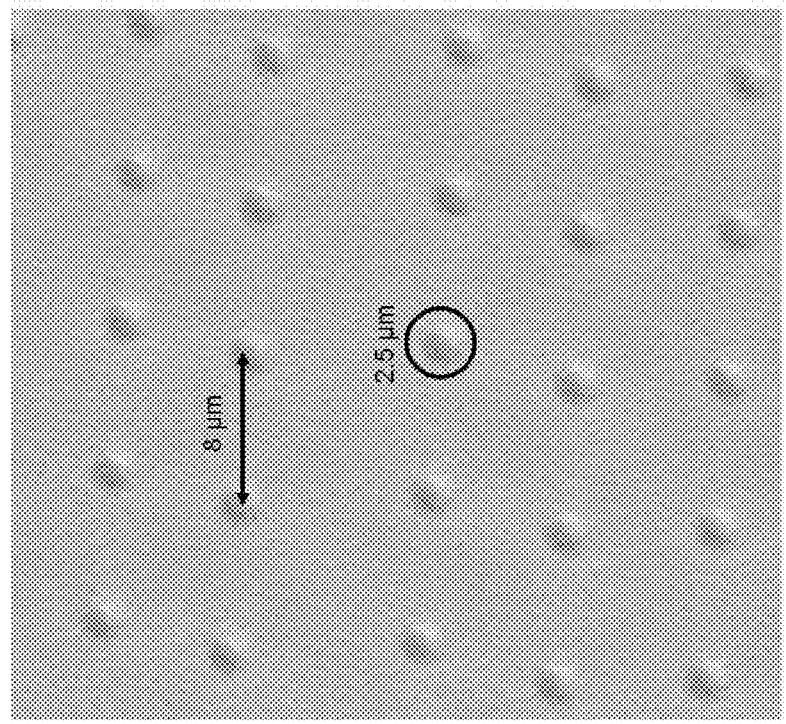
FIG. 23 shows an example of reference marks created by a surgical laser beam on a glass surface.

FIG. 23 shows examples of actual damage zones produced by a femtosecond laser in glass. The separation between the damage zones is on average 8 µm (the pulse energy is 2.2 µJ with duration of 580 fs at full width at half maximum). The optical damage depicted in FIG. 23 shows that the damage zones created by the femtosecond laser are well-defined and discrete. In the example shown, the damage zones have a diameter of about 2.5 µm. Optical damage zones similar to that shown in FIG. 22 are created in the phantom at various depths to form a 3-D array of the reference marks. These damage zones are referenced against the calibrated phantom either by extracting the appropriate disks and imaging it under a confocal microscope (FIG. 21A) or by splitting the phantom into two halves and measuring the depth using a micrometer (FIG. 21C). The x- and y-coordinates can be established from the pre-calibrated grid.

After damaging the phantom with the surgical laser, OCT on the phantom is performed. The OCT imaging system provides a 3D rendering of the phantom establishing a relationship between the OCT coordinate system and the phantom. The damage zones are detectable with the imaging system. The OCT and laser may be cross-calibrated using the phantom's internal standard. After the OCT and the laser are referenced against each other, the phantom can be discarded.

Prior to surgery, the calibration can be verified. This verification step involves creating optical damage at various positions inside of a second phantom. The optical damage should be intense enough such that the multiple damage zones which create a circular pattern can be imaged by the OCT. After the pattern is created, the second phantom is imaged with the OCT. Comparison of the OCT image with the laser coordinates provides the final check of the system calibration prior to surgery.

Once the coordinates are fed into the laser, laser surgery can be performed inside the eye. This involves photo-emulsification of the lens using the laser, as well as other laser treatments to the eye. The surgery can be stopped at any time and the anterior segment of the eye (FIG. 19) can be re-imaged to monitor the progress of the surgery; moreover, after an intraocular lens (IOL) is inserted, imaging the IOL (with light or no applanation) provides information regarding the position of the IOL in the eye. This information may be utilized by the physician to refine the position of IOL.

Figure 24:
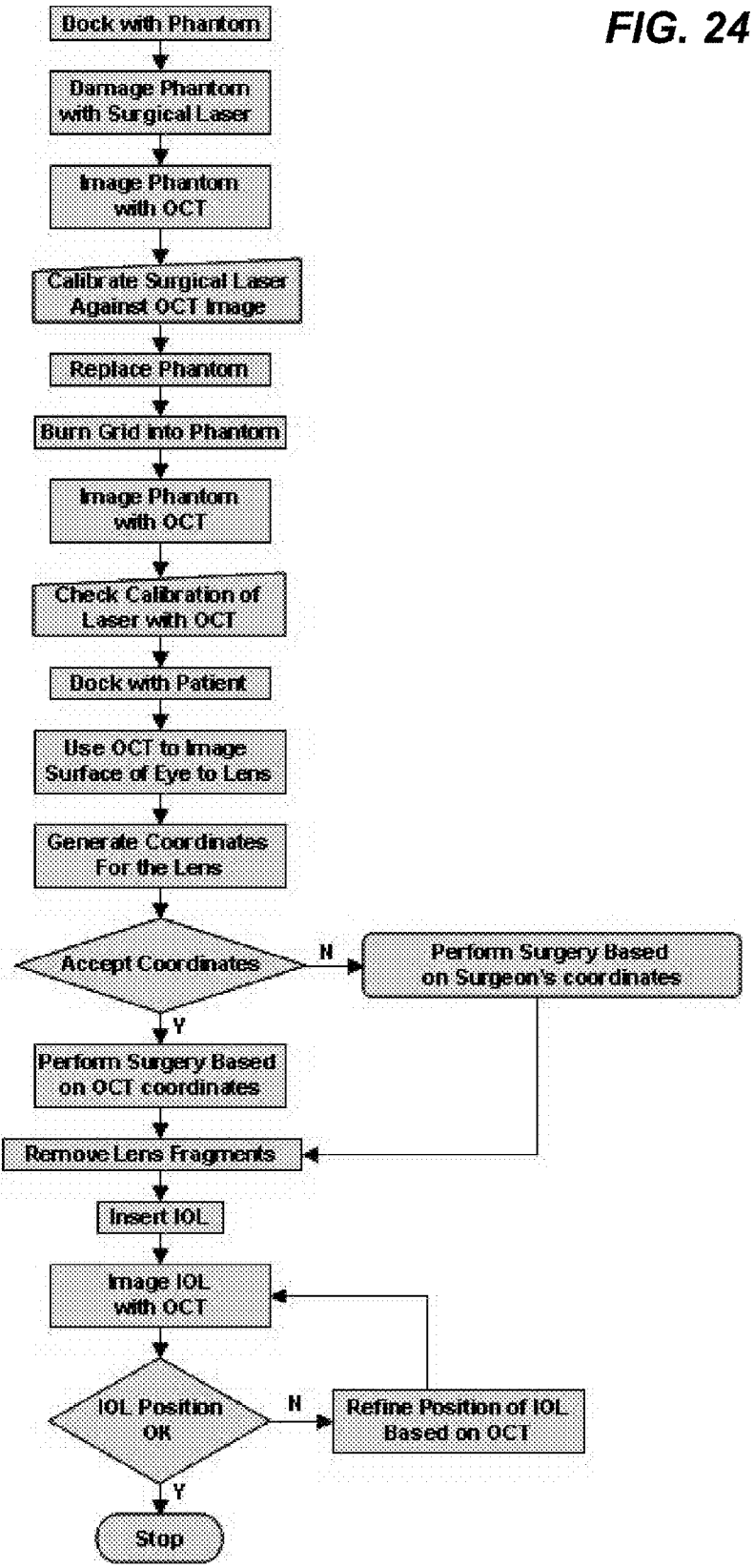
FIG. 24 shows an example of the calibration process and the post-calibration surgical operation for an imaging-guided laser surgical system.

FIG. 24 shows an example of the calibration process and the post-calibration surgical operation. This examples illustrates a method for performing laser surgery by using an imaging-guided laser surgical system can include using a patient interface in the system, that is engaged to hold a target tissue under surgery in position, to hold a calibration sample material during a calibration process before performing a surgery; directing a surgical laser beam of laser pulses from a laser in the system to the patient interface into the calibration sample material to burn reference marks at selected three-dimensional reference locations; directing an optical probe beam from an optical coherence tomography (OCT) module in the system to the patient interface into the calibration sample material to capture OCT images of the burnt reference marks; and establishing a relationship between positioning coordinates of the OCT module and the burnt reference marks. After the establishing the relationship, a patient interface in the system is used to engage to and to hold a target tissue under surgery in position. The surgical laser beam of laser pulses and the optical probe beam are directed to the patient interface into the target tissue. The surgical laser beam is controlled to perform laser surgery in the target tissue. The OCT module is operated to obtain OCT images inside the target tissue from light of the optical probe beam returning from the target tissue and the position information in the obtained OCT images and the established relationship are applied in focusing and scanning of the surgical laser beam to adjust the focusing and scanning of the surgical laser beam in the target tissue during surgery. While such calibrations can be performed immediately prior to laser surgery, they can also be performed at various intervals before a procedure, using calibration validations that demonstrated a lack of drift or change in calibration during such intervals.

The following examples describe imaging-guided laser surgical techniques and systems that use images of laser-induced photodisruption byproducts for alignment of the surgical laser beam.

Figure 25A:
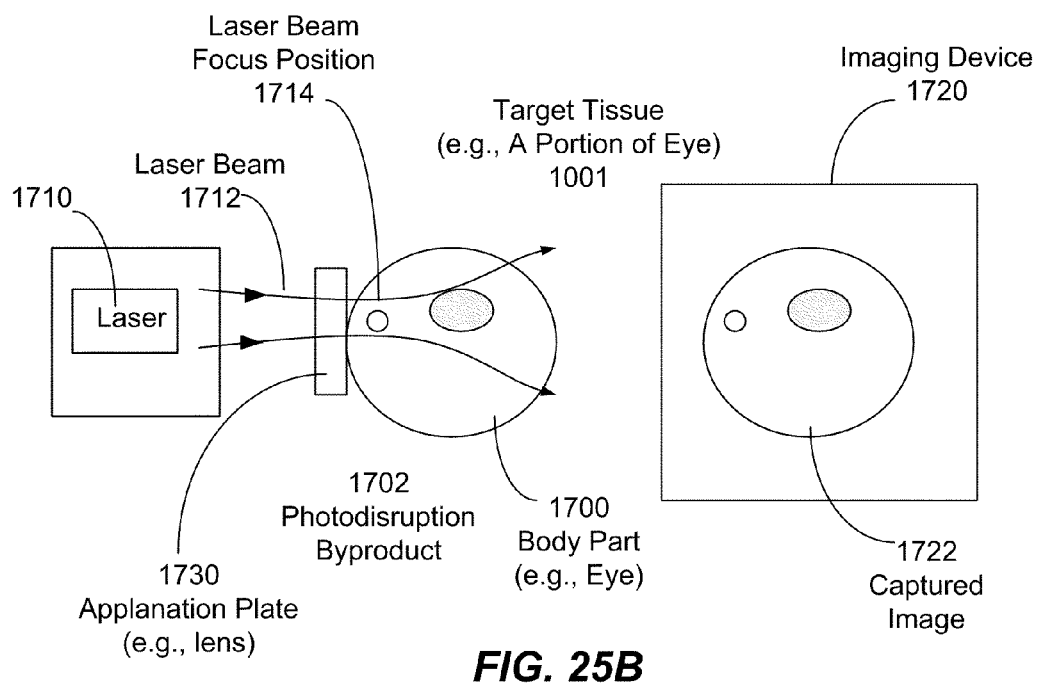
FIGS. 25A and 25B show two operation modes of an exemplary imaging-guided laser surgical system that captures images of laser-induced photodisruption byproduct and the target issue to guide laser alignment.
Figure 25B:
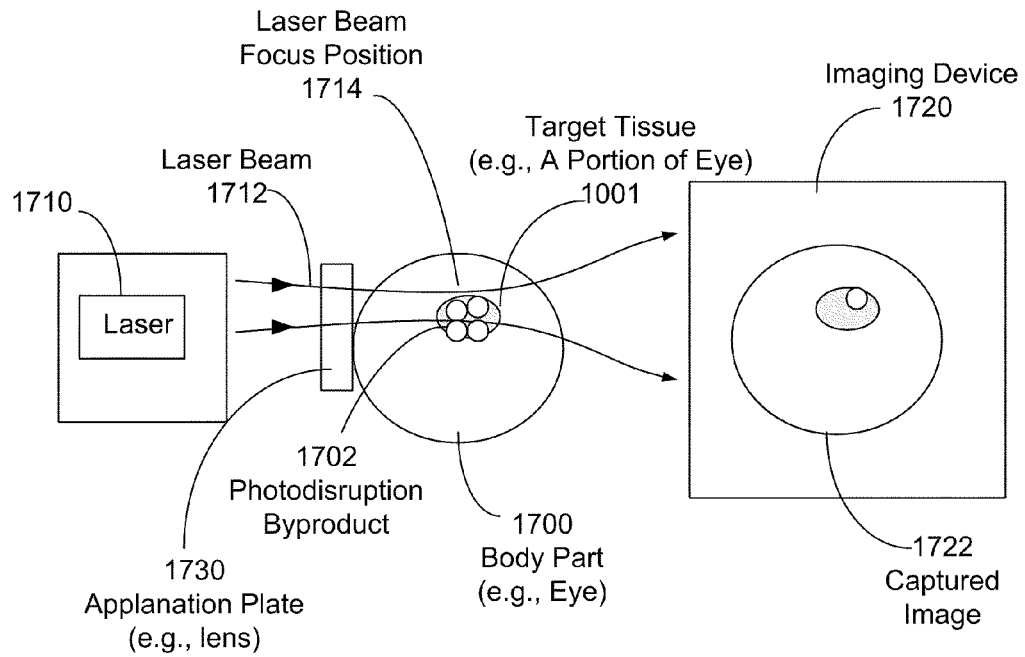

FIGS. 25A and 25B illustrates another implementation of the present technique in which actual photodisruption byproducts in the target tissue are used to guide further laser placement. A pulsed laser 1710, such as a femtosecond or picosecond laser, is used to produce a laser beam 1712 with laser pulses to cause photodisruption in a target tissue 1001. The target tissue 1001 may be a part of a body part 1700 of a subject, e.g., a portion of the lens of one eye. The laser beam 1712 is focused and directed by an optics module for the laser 1710 to a target tissue position in the target tissue 1001 to achieve a certain surgical effect. The target surface is optically coupled to the laser optics module by an applanation plate 1730 that transmits the laser wavelength, as well as image wavelengths from the target tissue. The applanation plate 1730 can be an applanation lens. An imaging device 1720 is provided to collect reflected or scattered light or sound from the target tissue 1001 to capture images of the target tissue 1001 either before or after (or both) the applanation plate is applied. The captured imaging data is then processed by the laser system control module to determine the desired target tissue position. The laser system control module moves or adjusts optical or laser elements based on standard optical models to ensure that the center of photodisruption byproduct 1702 overlaps with the target tissue position. This can be a dynamic alignment process where the images of the photodisruption byproduct 1702 and the target tissue 1001 are continuously monitored during the surgical process to ensure that the laser beam is properly positioned at each target tissue position.

In one implementation, the laser system can be operated in two modes: first in a diagnostic mode in which the laser beam 1712 is initially aligned by using alignment laser pulses to create photodisruption byproduct 1702 for alignment and then in a surgical mode where surgical laser pulses are generated to perform the actual surgical operation. In both modes, the images of the disruption byproduct 1702 and the target tissue 1001 are monitored to control the beam alignment. FIG. 25A shows the diagnostic mode where the alignment laser pulses in the laser beam 1712 may be set at a different energy level than the energy level of the surgical laser pulses. For example, the alignment laser pulses may be less energetic than the surgical laser pulses but sufficient to cause significant photodisruption in the tissue to capture the photodisruption byproduct 1702 at the imaging device 1720. The resolution of this coarse targeting may not be sufficient to provide desired surgical effect. Based on the captured images, the laser beam 1712 can be aligned properly. After this initial alignment, the laser 1710 can be controlled to produce the surgical laser pulses at a higher energy level to perform the surgery. Because the surgical laser pulses are at a different energy level than the alignment laser pulses, the nonlinear effects in the tissue material in the photodisruption can cause the laser beam 1712 to be focused at a different position from the beam position during the diagnostic mode. Therefore, the alignment achieved during the diagnostic mode is a coarse alignment and additional alignment can be further performed to precisely position each surgical laser pulse during the surgical mode when the surgical laser pulses perform the actual surgery. Referring to FIG. 25A, the imaging device 1720 captures the images from the target tissue 1001 during the surgical mode and the laser control module adjust the laser beam 1712 to place the focus position 1714 of the laser beam 1712 onto the desired target tissue position in the target tissue 1001. This process is performed for each target tissue position.

Figure 26:
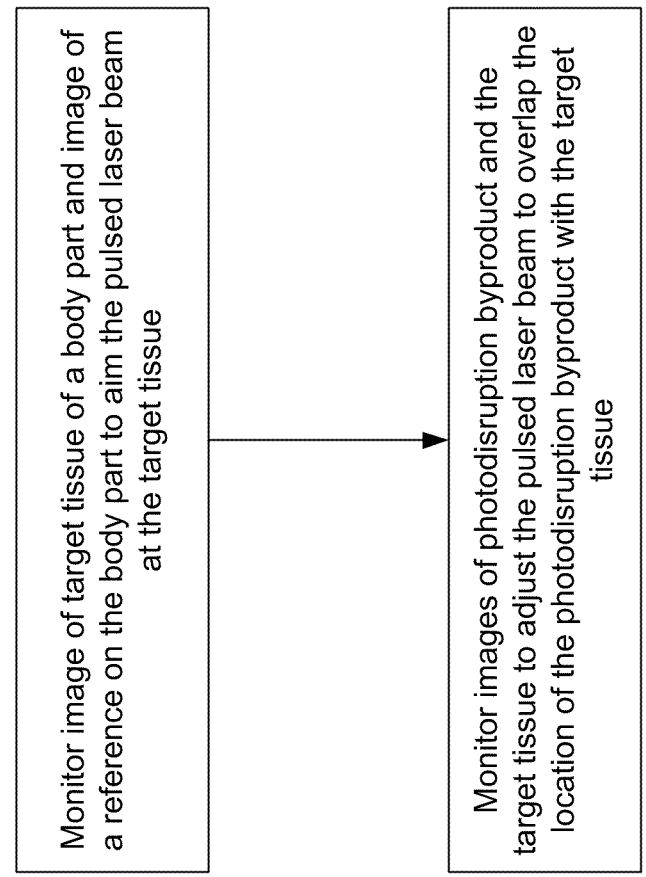
FIGS. 26 and 27 show examples of laser alignment operations in imaging-guided laser surgical systems.

FIG. 26 shows one implementation of the laser alignment where the laser beam is first approximately aimed at the target tissue and then the image of the photodisruption byproduct is captured and used to align the laser beam. The image of the target tissue of the body part as the target tissue and the image of a reference on the body part are monitored to aim the pulsed laser beam at the target tissue. The images of photodisruption byproduct and the target tissue are used to adjust the pulsed laser beam to overlap the location of the photodisruption byproduct with the target tissue.

Figure 27:
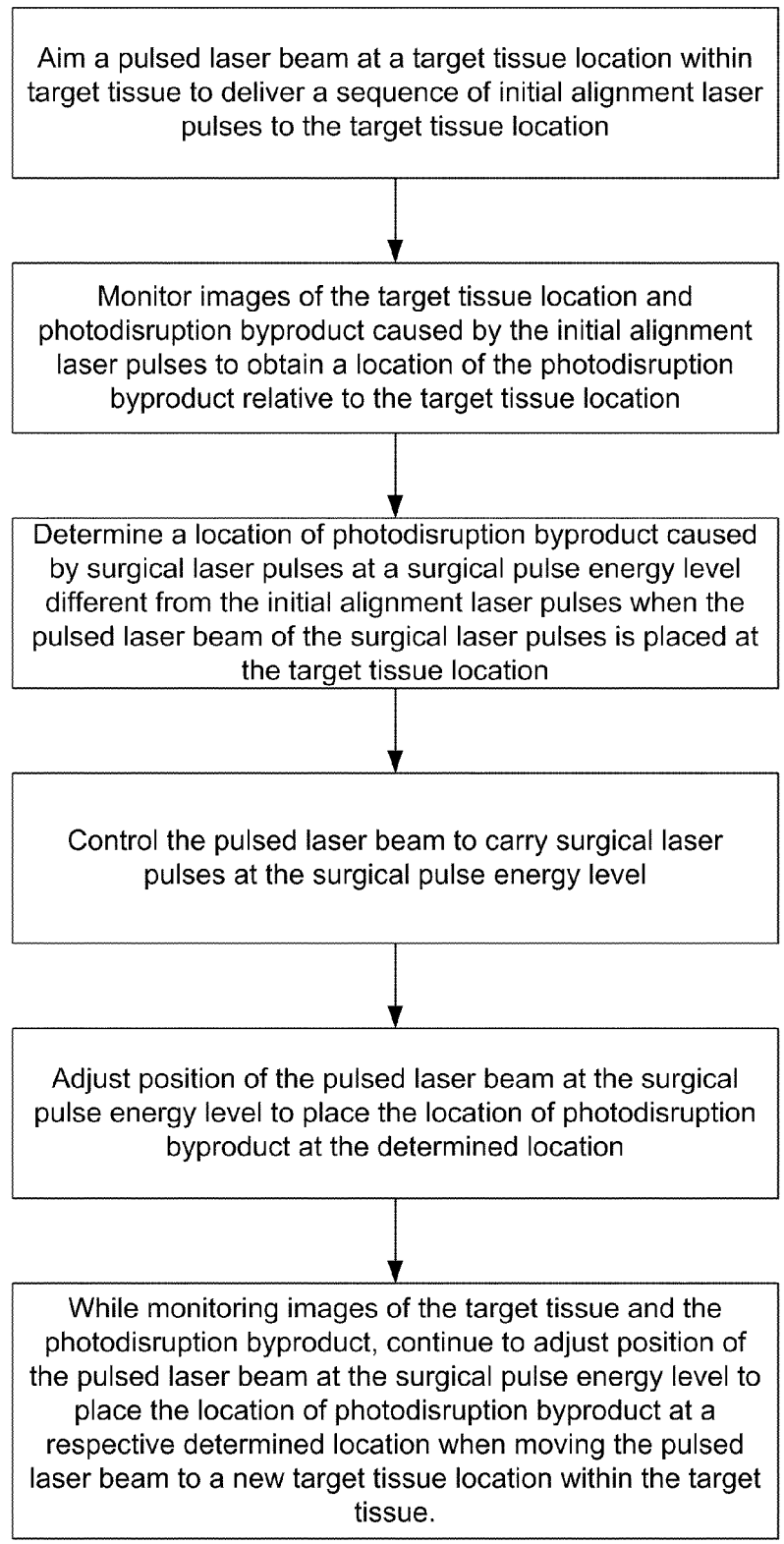

FIG. 27 shows one implementation of the laser alignment method based on imaging photodisruption byproduct in the target tissue in laser surgery. In this method, a pulsed laser beam is aimed at a target tissue location within target tissue to deliver a sequence of initial alignment laser pulses to the target tissue location. The images of the target tissue location and photodisruption byproduct caused by the initial alignment laser pulses are monitored to obtain a location of the photodisruption byproduct relative to the target tissue location. The location of photodisruption byproduct caused by surgical laser pulses at a surgical pulse energy level different from the initial alignment laser pulses is determined when the pulsed laser beam of the surgical laser pulses is placed at the target tissue location. The pulsed laser beam is controlled to carry surgical laser pulses at the surgical pulse energy level. The position of the pulsed laser beam is adjusted at the surgical pulse energy level to place the location of photodisruption byproduct at the determined location. While monitoring images of the target tissue and the photodisruption byproduct, the position of the pulsed laser beam at the surgical pulse energy level is adjusted to place the location of photodisruption byproduct at a respective determined location when moving the pulsed laser beam to a new target tissue location within the target tissue.

Figure 28:
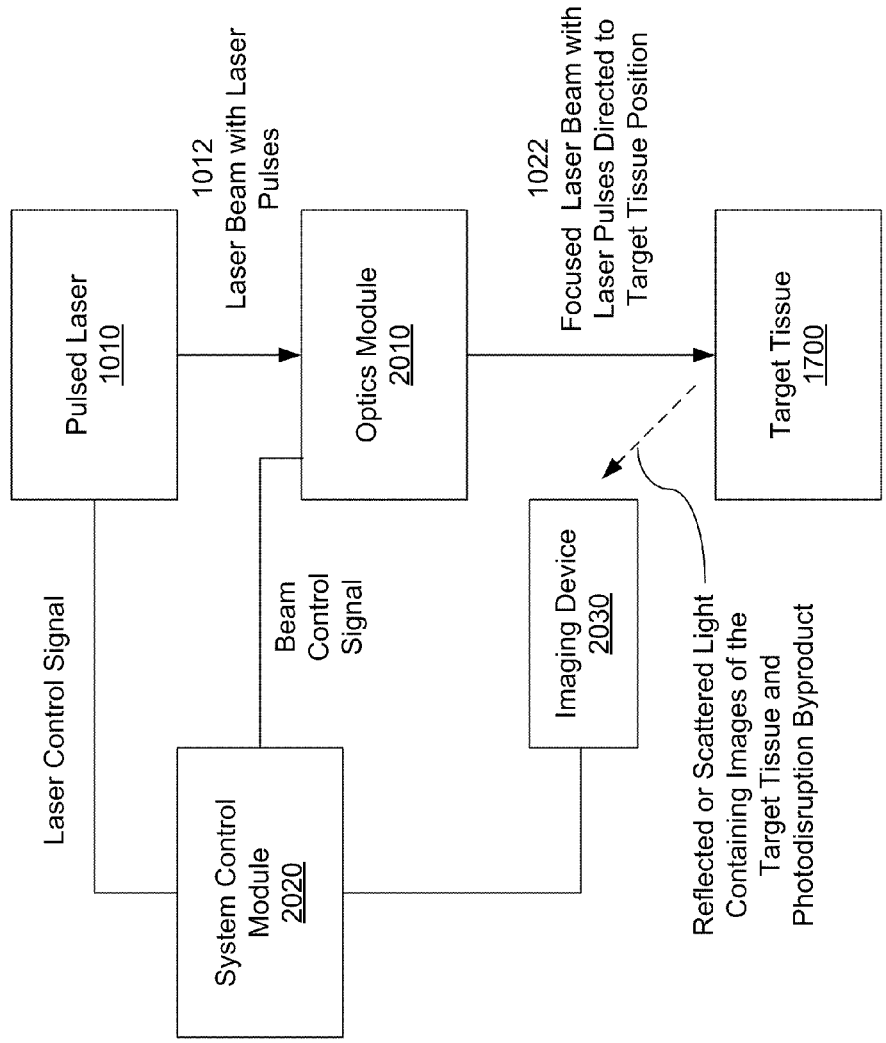
FIG. 28 shows an exemplary laser surgical system based on the laser alignment using the image of the photodisruption byproduct.

FIG. 28 shows an exemplary laser surgical system based on the laser alignment using the image of the photodisruption byproduct. An optics module 2010 is provided to focus and direct the laser beam to the target tissue 1700. The optics module 2010 can include one or more lenses and may further include one or more reflectors. A control actuator is included in the optics module 2010 to adjust the focusing and the beam direction in response to a beam control signal. A system control module 2020 is provided to control both the pulsed laser 1010 via a laser control signal and the optics module 2010 via the beam control signal. The system control module 2020 processes image data from the imaging device 2030 that includes the position offset information for the photodisruption byproduct 1702 from the target tissue position in the target tissue 1700. Based on the information obtained from the image, the beam control signal is generated to control the optics module 2010 which adjusts the laser beam. A digital processing unit is included in the system control module 2020 to perform various data processing for the laser alignment.

The imaging device 2030 can be implemented in various forms, including an optical coherent tomography (OCT) device. In addition, an ultrasound imaging device can also be used. The position of the laser focus is moved so as to place it grossly located at the target at the resolution of the imaging device. The error in the referencing of the laser focus to the target and possible non-linear optical effects such as self focusing that make it difficult to accurately predict the location of the laser focus and subsequent photodisruption event. Various calibration methods, including the use of a model system or software program to predict focusing of the laser inside a material can be used to get a coarse targeting of the laser within the imaged tissue. The imaging of the target can be performed both before and after the photodisruption. The position of the photodisruption by products relative to the target is used to shift the focal point of the laser to better localize the laser focus and photodisruption process at or relative to the target. Thus the actual photodisruption event is used to provide a precise targeting for the placement of subsequent surgical pulses.

Photodisruption for targeting during the diagnostic mode can be performed at a lower, higher or the same energy level that is required for the later surgical processing in the surgical mode of the system. A calibration may be used to correlate the localization of the photodisruptive event performed at a different energy in diagnostic mode with the predicted localization at the surgical energy because the optical pulse energy level can affect the exact location of the photodisruptive event. Once this initial localization and alignment is performed, a volume or pattern of laser pulses (or a single pulse) can be delivered relative to this positioning. Additional sampling images can be made during the course of delivering the additional laser pulses to ensure proper localization of the laser (the sampling images may be obtained with use of lower, higher or the same energy pulses). In one implementation, an ultrasound device is used to detect the cavitation bubble or shock wave or other photodisruption byproduct. The localization of this can then be correlated with imaging of the target, obtained via ultrasound or other modality. In another embodiment, the imaging device is simply a biomicroscope or other optical visualization of the photodisruption event by the operator, such as optical coherence tomography. With the initial observation, the laser focus is moved to the desired target position, after which a pattern or volume of pulses is delivered relative to this initial position.

As a specific example, a laser system for precise subsurface photodisruption can include means for generating laser pulses capable of generating photodisruption at repetition rates of 100-1000 Million pulses per second, means for coarsely focusing laser pulses to a target below a surface using an image of the target and a calibration of the laser focus to that image without creating a surgical effect, means for detecting or visualizing below a surface to provide an image or visualization of a target the adjacent space or material around the target and the byproducts of at least one photodisruptive event coarsely localized near the target, means for correlating the position of the byproducts of photodisruption with that of the sub surface target at least once and moving the focus of the laser pulse to position the byproducts of photodisruption at the sub surface target or at a relative position relative to the target, means for delivering a subsequent train of at least one additional laser pulse in pattern relative to the position indicated by the above fine correlation of the byproducts of photodisruption with that of the sub surface target, and means for continuing to monitor the photodisruptive events during placement of the subsequent train of pulses to further fine tune the position of the subsequent laser pulses relative to the same or revised target being imaged.

The above techniques and systems can be used deliver high repetition rate laser pulses to subsurface targets with a precision required for contiguous pulse placement, as needed for cutting or volume disruption applications. This can be accomplished with or without the use of a reference source on the surface of the target and can take into account movement of the target following applanation or during placement of laser pulses.

While this specification described various embodiments and implementations, these should not be construed as limitations on the scope of an invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

A number of implementations of laser surgical techniques, apparatus and systems are disclosed. However, variations and enhancements of the described implementations, and other implementations can be made based on what is described and illustrated.

What is claimed is:

1. An ophthalmic surgical method, the method comprising:
    determining a surgical target region in an eye;
    selecting a protection region between the surgical target region and a photosensitive tissue located distal to the surgical target region;
    estimating a damage-threshold of the photosensitive tissue and a protection-threshold of the protection region;
    applying preliminary laser-pulses to the protection region with parameters between the damage-threshold and the protection threshold at a focus spot of the laser pulses to form a protection barrier;
    applying surgical laser pulses to the surgical target region with at least one parameter above the damage threshold;
    wherein the estimating the damage-threshold of the photosensitive tissue comprises: estimating damage-threshold laser parameters, wherein laser pulses applied with the damage-threshold laser parameters are capable of damaging the photosensitive tissue; and
    wherein the estimating the protection-threshold of the protection region comprises: estimating protection-threshold laser parameters, wherein laser pulses applied with the protection-threshold laser parameters are capable of forming a protection barrier in the protection region.

2. The method of claim 1, wherein the selecting the protection region comprises:
    selecting a location and shape of the protection region so that a protection barrier formed in the protection region is capable of protecting the photosensitive tissue from damage by residual surgical laser pulses.

3. The method of claim 2, wherein the protecting the photosensitive tissue comprises at least one of:
    blocking, scattering, or absorbing the residual surgical laser pulses.

4. The method of claim 1, wherein the selecting the protection region comprises:
    determining a portion of a boundary of a nucleus of the eye.

5. The method of claim 1, wherein the estimating the protection-threshold and the damage-threshold comprises at least one of:
    analyzing characteristics of elements of a surgical laser system, preparatory and pre-operative measurements, observations of the eye of the patient, using calculations, using an age-based algorithm, using data obtained form cadaver experiments, and consulting data-bases.

6. The method of claim 1, wherein the estimating the damage-threshold and the protection-threshold comprises:
    estimating a laser pulse energy in the range of 0.5 microJ to 50 microJ;
    estimating a laser pulse energy density at a focus point of the laser pulses in the range of $6\times10^{-3}$ microJ/micron$^2$ to 60 microJ/micron$^2$;
    estimating a duration of a laser pulse in the range of 0.01 picoseconds to 50 picoseconds;
    estimating a frequency of applying laser pulses in the range of 10 kHz to 100 MHz; and
    estimating a separation distance of target regions of laser pulses in the range of 1 micron to 50 microns.

7. An eye-surgery method, the method comprising:
    identifying a portion of a boundary of a nucleus in a lens of an eye;
    estimating a damage-threshold of a retina and a protection-threshold of the nucleus;
    applying preliminary laser pulses with laser parameters between the damage-threshold and the protection-threshold at a focal spot of the laser pulses to a protection region in a posterior region of the nucleus to form a protection barrier;
    applying surgical laser pulses to a target region anterior to the protection barrier in the nucleus with at least one parameter above the damage-threshold;
    wherein the estimating the damage-threshold of the retina comprises: estimating damage-threshold laser parameters, wherein laser pulses applied with the damage-threshold laser parameters are capable of damaging the retina;
    wherein the estimating the protection-threshold of the nucleus comprises: estimating protection-threshold laser parameters, wherein laser pulses applied with the protection-threshold laser parameters to the protection region are capable of forming a protection barrier; and
    wherein the applying the preliminary laser pulses comprises: applying the preliminary laser pulses with laser parameters ensuring that the preliminary laser pulses damage the retina only to an insubstantial degree; and forming the protection barrier so situated and shaped that it is capable of protecting the retina from residual surgical laser pulses.

8. The method of claim 7, the identifying the portion of the boundary of the nucleus comprising:
    generating spaced-apart probe-bubbles inside the lens;
    observing a property of the generated probe-bubbles; and
    identifying the portion of the boundary in connection to the observed property of the probe-bubbles.

9. The method of claim 8, wherein:
    the observing a property of the generated bubbles comprises:
        identifying one or more probe-bubbles exhibiting a first growth rate; and identifying one or more probe-bubbles exhibiting a second growth rate different from the first growth rate; and the identifying the portion of the boundary comprises:
identifying a boundary between the probe-bubbles exhibiting the first growth rate and the probe-bubbles exhibiting the second growth rate.

10. The method of claim 8, wherein:
the observing a property of the generated probe-bubbles comprises:
applying ultrasound to the lens;
identifying one or more probe-bubbles exhibiting a first response to the ultrasound; and
identifying one or more probe-bubbles exhibiting a second response different from the first response; and
the identifying the portion of the boundary comprises:
identifying a boundary between the probe-bubbles exhibiting the first response and the probe-bubbles exhibiting the second response.

11. The method of claim 8, wherein the identifying the boundary comprises at least one of:
observing the probe-bubbles with an optical imaging method; and
observing the probe-bubbles with an optical coherence tomography.

12. The method of claim 7, wherein the estimating a protection-threshold and a damage-threshold comprises at least one of:
analyzing characteristics of elements of a surgical laser system, preparatory and pre-operative measurements, observations of the eye of the patient, using calculations, using an age-based algorithm, cadaver experiments, and consulting data-bases.

13. The method of claim 7, wherein the estimating the damage-threshold and the protection-threshold comprises:
estimating a laser pulse energy in the range of 0.5 microJ to 50 microJ;
estimating a laser pulse energy density at a focus point of the laser pulses in the range of $6 \times 10^{-3}$ microJ/micron$^2$ to 60 microJ/micron$^2$;
estimating a duration of a laser pulse in the range of 0.01 picoseconds to 50 picoseconds;
estimating a frequency of applying laser pulses in the range of 10 kHz to 100 MHz; and
estimating a separation distance of target regions of laser pulses in the range of 1 micron to 50 microns.

14. The method of claim 7, wherein the applying surgical laser pulses comprises at least one of:
disrupting, fragmenting, and emulsifying a portion of the nucleus.

15. A surgical method for protecting a photosensitive tissue distal to a target of photodisruption, the method comprising:
determining a surgical target region in a body of a subject;
selecting a protection region between the surgical target region and the photosensitive tissue;
estimating a damage-threshold of the photosensitive tissue and a protection-threshold of the protection region;
applying preliminary laser-pulses to the protection region with parameters between the damage-threshold and the protection threshold at a focal spot of the laser pulses to form a protection barrier;
applying surgical laser pulses to the surgical target region with at least one parameter above the damage-threshold;
wherein the estimating the damage-threshold of the photosensitive tissue comprises: estimating damage-threshold laser parameters, wherein laser pulses applied with the damage-threshold laser parameters are capable of damaging the photosensitive tissue; and
wherein the estimating the protection-threshold of the protection region comprises: estimating protection-threshold laser parameters, wherein laser pulses applied with the protection-threshold laser parameters are capable of forming a protection barrier in the protection region.

* * * * *